United States Patent
Heath et al.

(10) Patent No.: US 11,168,115 B2
(45) Date of Patent: Nov. 9, 2021

(54) CYCLIC PEPTIDES AS PROTEIN TARGETING AGENTS

(71) Applicant: California Institute of Technology, Pasadena, CA (US)

(72) Inventors: James R. Heath, South Pasadena, CA (US); Rosemary Dyane Rohde, Pasadena, CA (US); Arundhati Nag, Pasadena, CA (US); Samir Das, Pasadena, CA (US); Aiko Umeda, North Hollywood, CA (US)

(73) Assignee: CALIFORNIA INSTITUTE OF TECHNOLOGY, Pasadena, CA (US)

(*) Notice: Subject to any disclaimer, the term of this patent is extended or adjusted under 35 U.S.C. 154(b) by 351 days.

(21) Appl. No.: 14/310,201

(22) Filed: Jun. 20, 2014

(65) Prior Publication Data
US 2015/0078999 A1 Mar. 19, 2015

Related U.S. Application Data

(60) Provisional application No. 61/837,556, filed on Jun. 20, 2013, provisional application No. 61/925,058, filed on Jan. 8, 2014.

(51) Int. Cl.
| | |
|---|---|
| *C07K 7/64* | (2006.01) |
| *A61K 51/08* | (2006.01) |
| *A61K 49/00* | (2006.01) |
| *C07K 5/06* | (2006.01) |
| *C07K 5/08* | (2006.01) |
| *C07K 1/04* | (2006.01) |
| *C07K 5/10* | (2006.01) |
| *C07K 7/56* | (2006.01) |
| *C07K 14/00* | (2006.01) |
| *G01N 33/573* | (2006.01) |
| *G01N 33/68* | (2006.01) |

(52) U.S. Cl.
CPC ............ *C07K 7/64* (2013.01); *A61K 49/0032* (2013.01); *A61K 49/0041* (2013.01); *A61K 49/0043* (2013.01); *A61K 51/08* (2013.01); *A61K 51/088* (2013.01); *C07K 1/047* (2013.01); *C07K 5/06* (2013.01); *C07K 5/08* (2013.01); *C07K 5/10* (2013.01); *C07K 7/56* (2013.01); *C07K 14/001* (2013.01); *G01N 33/573* (2013.01); *G01N 33/6842* (2013.01); *G01N 2333/912* (2013.01)

(58) Field of Classification Search
CPC .............. A61K 49/00; A61K 49/0032; A61K 49/0041; A61K 49/0043; A61K 51/00; A61K 51/08; A61K 51/088; C07K 1/047; C07K 5/06; C07K 5/08; C07K 5/10; C07K 7/56; C07K 7/64; C07K 14/001; G01N 33/573; G01N 33/682; G01N 2333/912; G01N 33/6842

USPC ........ 424/1.11, 1.65, 1.69, 9.1, 9.2, 9.3, 9.4, 424/9.5, 9.6; 514/1, 1.1; 530/300, 317, 530/326, 327, 328, 329, 330, 331
See application file for complete search history.

(56) References Cited

U.S. PATENT DOCUMENTS

2006/0008848 A1 1/2006 Verdine et al.

FOREIGN PATENT DOCUMENTS

| WO | 2012021874 A1 | 2/2012 |
|---|---|---|
| WO | 2013009869 A2 | 1/2013 |
| WO | 2014205317 A2 | 12/2014 |

OTHER PUBLICATIONS

Isaad et al, Journal of Peptide Science, 2009, vol. 15, pp. 451-454.*
Joo, Biomol. Ther., 2012, vol. 20, No. 1, pp. 19-26.*
Agnew et al. (Jun. 22, 2009) "Iterative In Situ Click Chemistry Creates Antibody-like Protein-Capture Agents," Angewandte Chemie. 48(27):4944-4948.
Brown et al. (Mar. 15, 2013) "Stapled Peptides with Improved Potency and Specificity That Activate p53," ACS Chemical Biology. 8(3):506-512.
Cantel et al. (Aug. 1, 2008) "Synthesis and Conformational Analysis of a Cyclic Peptide Obtained via i to i +4 Intramolecular Side-Chain to Side-Chain Azide-Alkyne 1,3-Dipolar Cycloaddition," The Journal of Organic Chemistry. 73(15):5663-5674.
Cochrane et al. (Jan. 1, 2013) "Investigation of the ring-closing metathesis of peptides in water," Organic & Biomolecular Chemistry. 11(4):630.

(Continued)

*Primary Examiner* — D. L. Jones
(74) *Attorney, Agent, or Firm* — Pabst Patent Group LLP

(57) ABSTRACT

Peptides having activity as protein binding agents are disclosed. The peptides have the following structure (I):

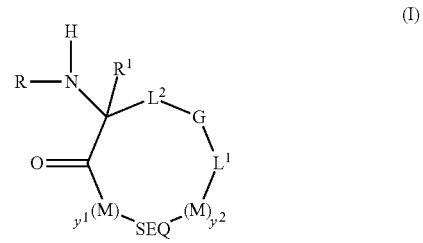

including stereoisomers, pharmaceutically acceptable salts and prodrugs thereof, wherein R, $R^1$, $L^1$, $L^2$, G, M, $Y^1$, $Y^2$ and SEQ are as defined herein. Methods associated with preparation and use of such peptides, as well as pharmaceutical compositions comprising such peptides, are also disclosed.

17 Claims, 13 Drawing Sheets

Specification includes a Sequence Listing.

(56) References Cited

OTHER PUBLICATIONS

Empting et al. (May 23, 2011) "Triazole Bridge: Disulfide-Bond Replacement by Ruthenium-Catalyzed Formation of 1,5-Disubstituted 1,2,3-Triazoles," Angewandte Chemie International Edition. 50(22):5207-5211.
Erlanson et al. (Aug. 15, 2000) "Site-directed ligand discovery," Proc Natl Acad Sci. 97(17):9367-9372.
Lam et al. (Nov. 7, 1991) "A new type of synthetic peptide library for identifying ligand-binding activity," Nature. 354(6348):82-84.
Manetsch et al. (Sep. 18, 2004) "In Situ Click Chemistry: Enzyme Inhibitors Made to Their Own Specifications," American Chemical Society. 126(40):12809-12818.
Mocharla et al. (Dec. 17, 2004) "In Situ Click Chemistry: Enzyme-Generated Inhibitors of Carbonic Anhydrase II," Angewandte Chemie. 44(1):116-120.
Murray et al. (Oct. 2002) "The consequences of translational and rotational entropy lost by small molecules on binding to proteins," Journal of Computer-Aided Molecular Design. 16(10):741-753.
Punna et al. (Apr. 8, 2005) "Head-to-tail peptide cyclodimerization by copper-catalyzed azide-alkyne Cycloaddition," Angewandte Chemie International Edition, Wiley-VCH Verlag Gmbh & Co, KGAA, DE. 44(15):2215-2220.
Scrima et al. (Jan. 1, 2010) "Cu I-Catalyzed Azide Alkyne Intramolecular i-to-( i +4) Side-Chain-to-Side-Chain Cyclization Promotes the Formation of Helix-Like Secondary Structures," European Journal of Organic Chemistry. 2010(3):446-457.
Shuker et al. (Nov. 29, 1996) "Discovering high-affinity ligands for proteins: SAR by NMR," Science. 274 (5292):1531-1534.
Tal-Gan et al. (Jul. 28, 2011) "Backbone Cyclic Peptide Inhibitors of Protein Kinase B (PKB/Akt)," Journal of Medicinal Chemistry, American Chemical Society. 54(14):5154-5164.
Whiting et al. (Feb. 20, 2006) "Inhibitors of HIV-1 Protease by Using In Situ Click Chemistry," Angewandte Chemie. 45(9):1435-1439.
International Search Report corresponding to International Patent Application No. PCT/US2014/043354, dated Sep. 22, 2014.

* cited by examiner

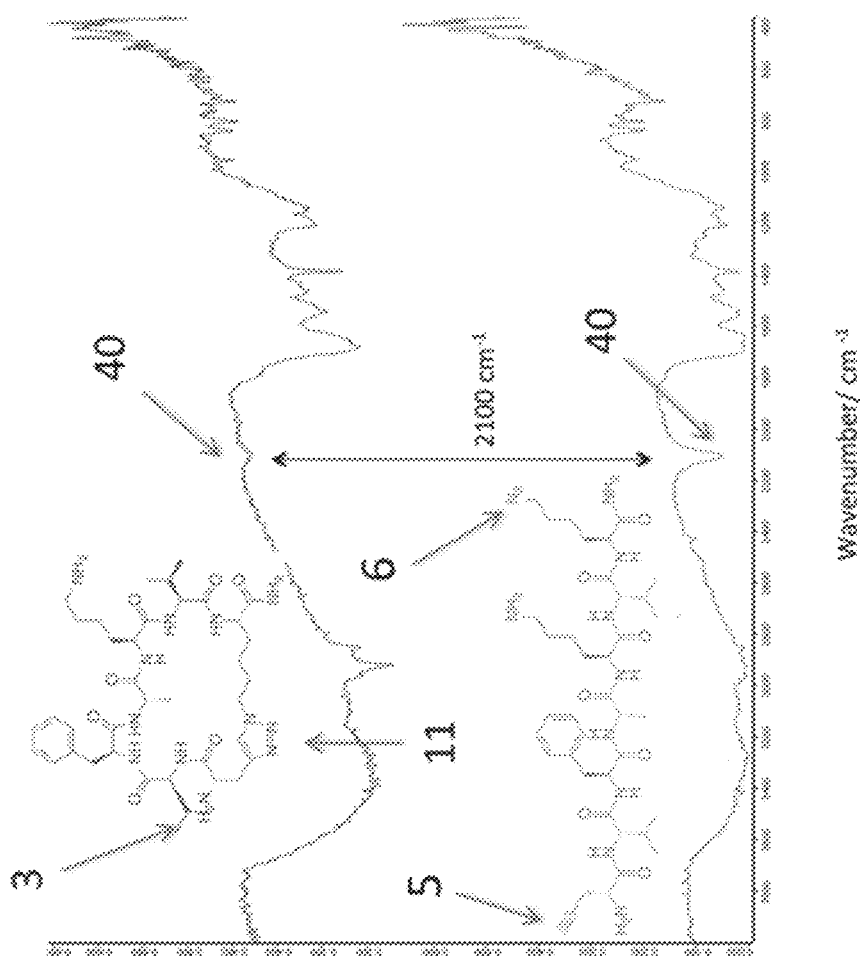
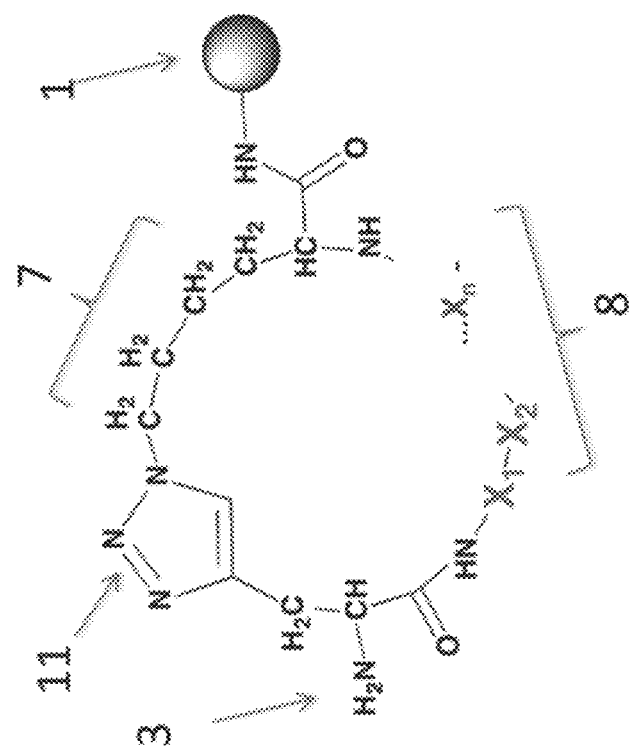
A: n = 7; diversity = 6x10^7; D amino acids
B: n=5; diversity = 2x10^6; $X_i$ D amino acid
C: n=5; diversity = 2x10^6; $X_i$ L amino acid
FIG. 4

Sequence of human Akt2

MNEVSVIKEG WLHKRGEYIK TWRPRYFLLK SDGSFIGYKE RPEAPDQTLP PLNNFSVAEC QLMKTERPRP
NTFVIRCLQW TTVIERTFHV DSPDEREEWM RAIQMVANSL APGEDPM DYKCGSPSDS STTEEMEVAV
SKARAKVTMN DFDYLKLLGK GTFGKVILVR EKATGRYYAM KILRKEVIIA KDEVAHTVTE SRVLQNTRHP
FLTALKYAFQ THDRLCFVME YANGGELFFH LSRERVFTEE RARFYGAEIV SALEYLHSRD VVYRDIKLEN
LMLDKDGHIK ITDFGLCKEG ISDGATMKTF CGTPEYLAPE VLEDNDYGRA VDWWGLGVVM EMMCGRLPF
NQDHERLFE LILMEEIRFP RTLSPEAKSL LAGLLKKDPK QRLGGGPSDA KEVMEHRFFL SINWQDVVQK
KLLPPFKPQV TSEVDTRYFD DEFTAQSITI TPPDRYDSLG LLELDQRTHF PQFSYSASIRE

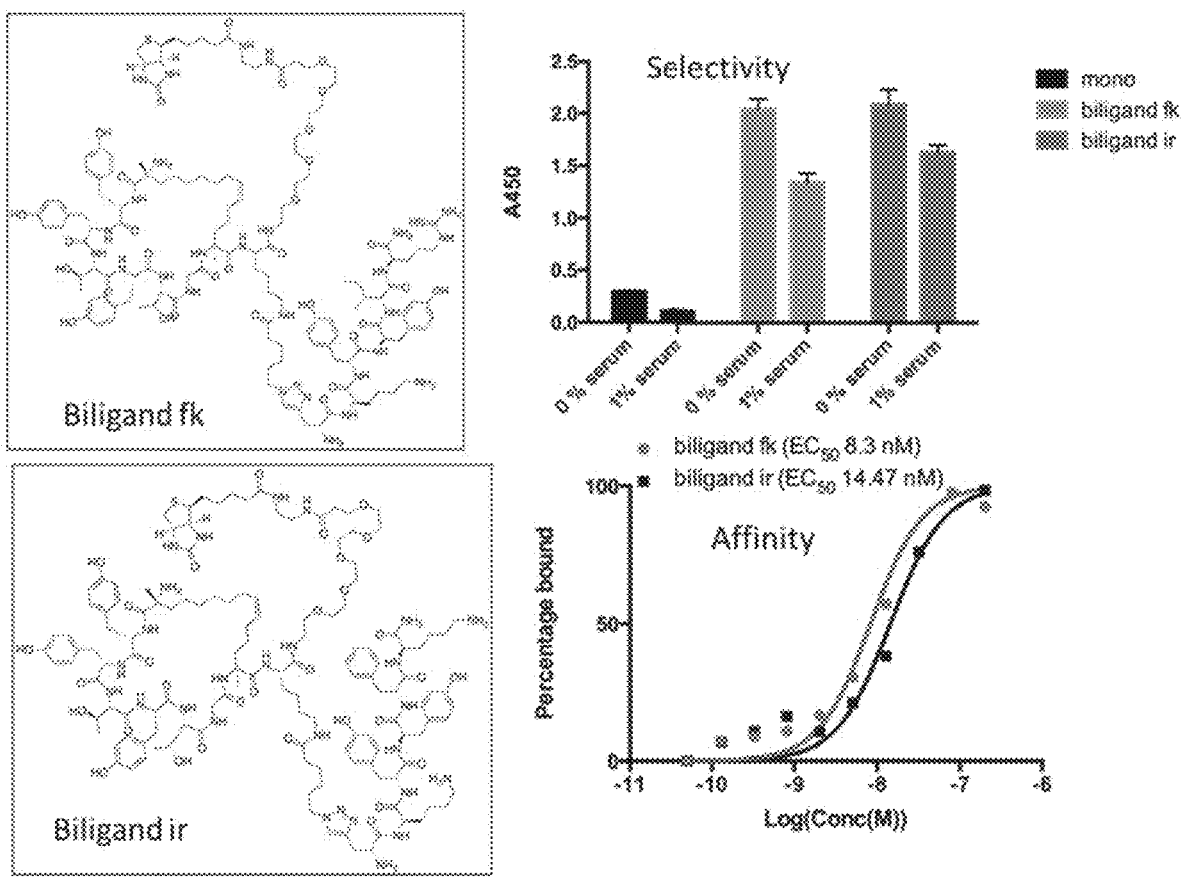

FIG. 7

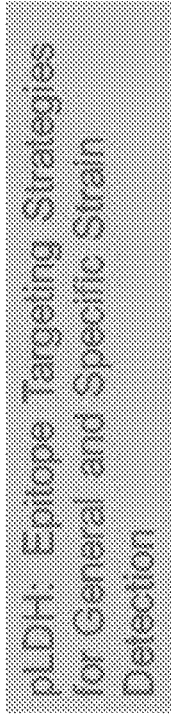
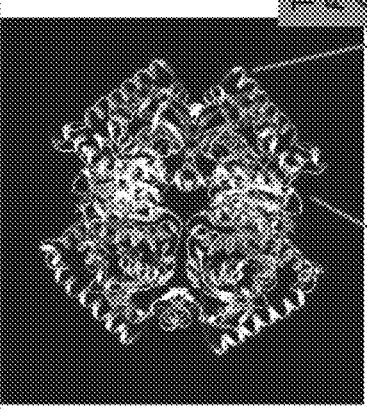
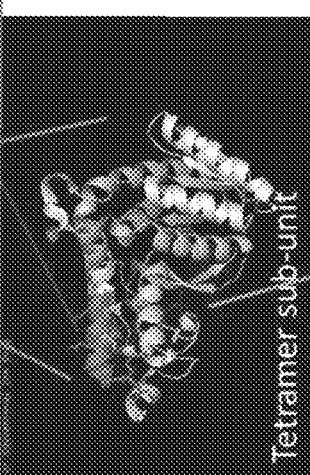
FIG. 8

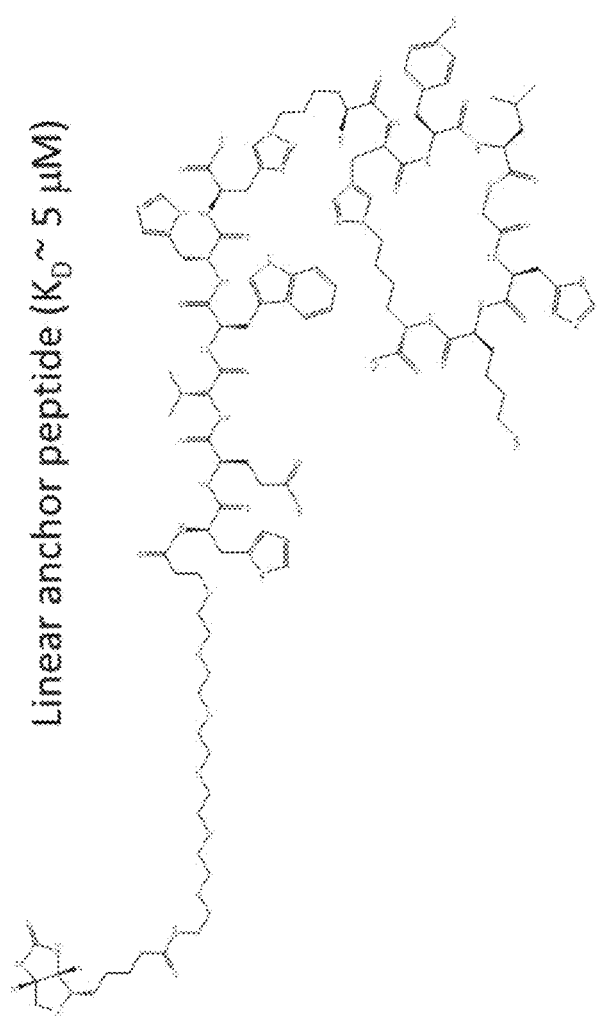
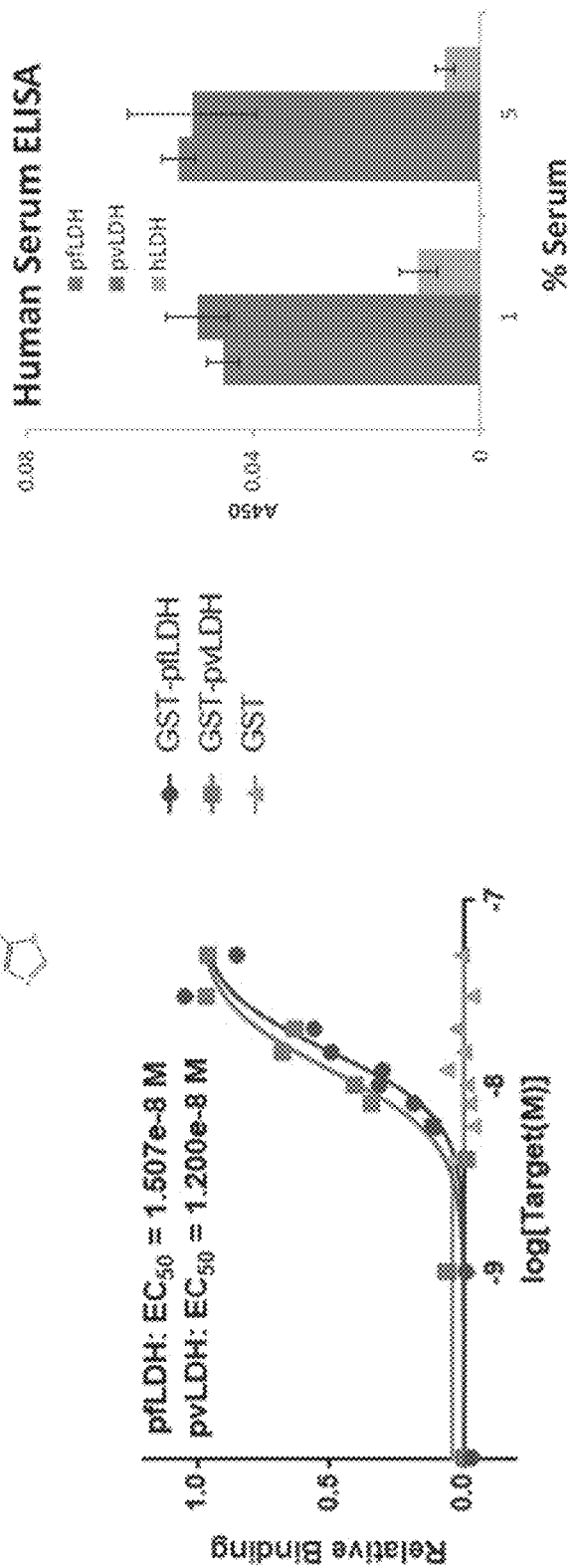
FIG. 12

SEQUENCE LISTING

<160> NUMBER OF SEQ ID NOS: 39

<210> SEQ ID NO 1
<211> LENGTH: 5
<212> TYPE: PRT
<213> ORGANISM: Artificial Sequence
<220> FEATURE:
<223> OTHER INFORMATION: Synthetic peptide selected to have an affinity
      for desired target, including allosteric binding sites
      such as peptide epitopes.

<400> SEQUENCE: 1

Tyr Val Tyr Lys Ser
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic peptide selected to have an affinity
      for desired target, including allosteric binding sites
      such as peptide epitopes.

<400> SEQUENCE: 2

Val Phe Ala Lys Val
1               5

```
<210> SEQ ID NO 3
<211> LENGTH: 5
<212> TYPE: PRT
<213> ORGANISM: Artificial Sequence
<220> FEATURE:
<223> OTHER INFORMATION: Synthetic peptide selected to have an affinity
      for desired target, including allosteric binding sites
      such as peptide epitopes.

<400> SEQUENCE: 3

Ile Arg Tyr Tyr Ser
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic peptide selected to have an affinity
      for desired target, including allosteric binding sites
      such as peptide epitopes.

<400> SEQUENCE: 4

Tyr Tyr Thr Tyr Thr
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic peptide selected to have an affinity
      for desired target, including allosteric binding sites
      such as peptide epitopes.

<400> SEQUENCE: 5

Arg Gly Gly Ile Leu
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic peptide selected to have an affinity
      for desired target, including allosteric binding sites
      such as peptide epitopes.

<400> SEQUENCE: 6

Lys Lys Ile His Leu
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic peptide selected to have an affinity
      for desired target, including allosteric binding sites
      such as peptide epitopes.

<400> SEQUENCE: 7

Ile Leu Tyr Trp Lys
1               5

<210> SEQ ID NO 8
<211> LENGTH: 5
<212> TYPE: PRT
```

```
<213> ORGANISM: Artificial Sequence
<220> FEATURE:
<223> OTHER INFORMATION: Synthetic peptide selected to have an affinity
      for desired target, including allosteric binding sites
      such as peptide epitopes.

<400> SEQUENCE: 8

Pro Leu Lys Lys Gly
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic peptide selected to have an affinity
      for desired target, including allosteric binding sites
      such as peptide epitopes.

<400> SEQUENCE: 9

Leu Lys Thr Gly Gln
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic peptide selected to have an affinity
      for desired target, including allosteric binding sites
      such as peptide epitopes.

<400> SEQUENCE: 10

Leu Lys Thr Gly Thr
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic peptide selected to have an affinity
      for desired target, including allosteric binding sites
      such as peptide epitopes.

<400> SEQUENCE: 11

His Trp Ser Ala Asn
1               5

<210> SEQ ID NO 12
<211> LENGTH: 4
<212> TYPE: PRT
<213> ORGANISM: Artificial Sequence
<220> FEATURE:
<223> OTHER INFORMATION: Synthetic peptide selected to have an affinity
      for desired target, including allosteric binding sites
      such as peptide epitopes.

<400> SEQUENCE: 12

Tyr Trp Gln Trp
1

<210> SEQ ID NO 13
<211> LENGTH: 6
<212> TYPE: PRT
<213> ORGANISM: Artificial Sequence
<220> FEATURE:
<223> OTHER INFORMATION: Synthetic peptide selected to have an affinity
      for desired target, including allosteric binding sites
``` such as peptide epitopes.

<400> SEQUENCE: 13

Gly His Trp Ser Ala Asn
1               5

<210> SEQ ID NO 14
<211> LENGTH: 5
<212> TYPE: PRT
<213> ORGANISM: Artificial Sequence
<220> FEATURE:
<223> OTHER INFORMATION: Synthetic peptide selected to have an affinity
      for desired target, including allosteric binding sites
      such as peptide epitopes.

<400> SEQUENCE: 14

Tyr Leu Gly His Lys
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic peptide selected to have an affinity
      for desired target, including allosteric binding sites
      such as peptide epitopes.

<400> SEQUENCE: 15

Leu Ala Tyr Pro Pro
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic peptide selected to have an affinity
      for desired target, including allosteric binding sites
      such as peptide epitopes.

<400> SEQUENCE: 16

Leu Ala Tyr Pro Ala
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic peptide selected to have an affinity
      for desired target, including allosteric binding sites
      such as peptide epitopes.

<400> SEQUENCE: 17

Leu Ala Tyr Ala Ala
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic peptide selected to have an affinity
      for desired target, including allosteric binding sites
      such as peptide epitopes.

<400> SEQUENCE: 18

```
Leu Ala Tyr Ala Pro
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic peptide selected to have an affinity
      for desired target, including allosteric binding sites
      such as peptide epitopes.

<400> SEQUENCE: 19

Glu Leu Tyr Lys Tyr
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic peptide selected to have an affinity
      for desired target, including allosteric binding sites
      such as peptide epitopes.

<400> SEQUENCE: 20

Gly Ile Phe Ala Val Thr
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic peptide selected to have an affinity
      for desired target, including allosteric binding sites
      such as peptide epitopes.

<400> SEQUENCE: 21

Gly Ile Val Gly Ala Pro
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic peptide selected to have an affinity
      for desired target, including allosteric binding sites
      such as peptide epitopes.

<400> SEQUENCE: 22

Gly Asn Trp Pro Ala Ala
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic peptide selected to have an affinity
      for desired target, including allosteric binding sites
      such as peptide epitopes.

<400> SEQUENCE: 23

Gly Phe Asn Val Asp Leu
1               5
```

```
<210> SEQ ID NO 24
<211> LENGTH: 6
<212> TYPE: PRT
<213> ORGANISM: Artificial Sequence
<220> FEATURE:
<223> OTHER INFORMATION: Synthetic peptide selected to have an affinity
      for desired target, including allosteric binding sites
      such as peptide epitopes.

<400> SEQUENCE: 24

Gly Trp Asn Val Asp Leu
1               5

<210> SEQ ID NO 25
<211> LENGTH: 6
<212> TYPE: PRT
<213> ORGANISM: Artificial Sequence
<220> FEATURE:
<223> OTHER INFORMATION: Synthetic peptide selected to have an affinity
      for desired target, including allosteric binding sites
      such as peptide epitopes.

<400> SEQUENCE: 25

Gly Ser Thr Glu Trp Leu
1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic peptide selected to have an affinity
      for desired target, including allosteric binding sites
      such as peptide epitopes.

<400> SEQUENCE: 26

Gly Ser Gln Glu Trp Leu
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic peptide selected to have an affinity
      for desired target, including allosteric binding sites
      such as peptide epitopes.

<400> SEQUENCE: 27

Gly Thr Glu Ser Val Ala
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic peptide selected to have an affinity
      for desired target, including allosteric binding sites
      such as peptide epitopes.

<400> SEQUENCE: 28

Gly Gln Ile Thr Ile Tyr
1               5

<210> SEQ ID NO 29
<211> LENGTH: 6
<212> TYPE: PRT
<213> ORGANISM: Artificial Sequence
```

```
<220> FEATURE:
<223> OTHER INFORMATION: Synthetic peptide selected to have an affinity
      for desired target, including allosteric binding sites
      such as peptide epitopes.

<400> SEQUENCE: 29

Gly Gln Ile Gln Ile Tyr
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic peptide selected to have an affinity
      for desired target, including allosteric binding sites
      such as peptide epitopes.

<400> SEQUENCE: 30

Gly Thr Ile Thr Ile Tyr
1               5

<210> SEQ ID NO 31
<211> LENGTH: 6
<212> TYPE: PRT
<213> ORGANISM: Artificial Sequence
<220> FEATURE:
<223> OTHER INFORMATION: Synthetic peptide selected to have an affinity
      for desired target, including allosteric binding sites
      such as peptide epitopes.

<400> SEQUENCE: 31

Gly Thr Ile Gln Ile Tyr
1               5

<210> SEQ ID NO 32
<211> LENGTH: 6
<212> TYPE: PRT
<213> ORGANISM: Artificial Sequence
<220> FEATURE:
<223> OTHER INFORMATION: Synthetic peptide selected to have an affinity
      for desired target, including allosteric binding sites
      such as peptide epitopes.

<400> SEQUENCE: 32

Gly Thr Ala Val Asn Ala
1               5

<210> SEQ ID NO 33
<211> LENGTH: 6
<212> TYPE: PRT
<213> ORGANISM: Artificial Sequence
<220> FEATURE:
<223> OTHER INFORMATION: Synthetic peptide selected to have an affinity
      for desired target, including allosteric binding sites
      such as peptide epitopes.

<400> SEQUENCE: 33

Gly Gln Ala Val Asn Ala
1               5

<210> SEQ ID NO 34
<211> LENGTH: 12
<212> TYPE: PRT
<213> ORGANISM: Artificial Sequence
<220> FEATURE:
<223> OTHER INFORMATION: Peptide epitope specific for the plasmodium
      falciparum LDH protein.
```

```
<400> SEQUENCE: 34

Leu Ile Ser Asp Ala Glu Leu Glu Ala Ile Phe Asp
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Peptide epitope specific for the plasmodium
      falciparum LDH protein.

<400> SEQUENCE: 35

Asp Asp Ile Ala Ile Leu Glu Glu Phe Ala Leu Ser
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Peptide epitope specific for the malarial
      parasite LDH protein.

<400> SEQUENCE: 36

Gly Val Glu Gln Val Ile Glu Leu Gln Leu Asn
1               5                   10

<210> SEQ ID NO 37
<211> LENGTH: 26
<212> TYPE: PRT
<213> ORGANISM: Artificial Sequence
<220> FEATURE:
<223> OTHER INFORMATION: Synthetic N-terminal sequence

<400> SEQUENCE: 37

Met Val Ser Phe Ser Lys Asn Lys Val Leu Ser Ala Ala Val Phe Ala
1               5                   10                  15

Ser Val Leu Leu Leu Asp Asn Asn Asn Ser
            20                  25

<210> SEQ ID NO 38
<211> LENGTH: 29
<212> TYPE: PRT
<213> ORGANISM: Artificial Sequence
<220> FEATURE:
<223> OTHER INFORMATION: Synthetic N-terminal sequence

<400> SEQUENCE: 38

Phe Asn Asn Asn Leu Cys Ser Lys Asn Ala Lys Gly Leu Asn Leu Asn
1               5                   10                  15

Lys Arg Leu Leu His Glu Thr Gln Ala His Val Asp Asp
            20                  25

<210> SEQ ID NO 39
<211> LENGTH: 20
<212> TYPE: PRT
<213> ORGANISM: Artificial Sequence
<220> FEATURE:
<223> OTHER INFORMATION: Synthetic C-terminal sequence
```

```
<400> SEQUENCE: 39

Ala His His Ala Thr Asp Ala His His Ala Ala Ala His His Glu Ala
1               5                   10                  15

Ala Thr His Cys
            20
```

CYCLIC PEPTIDES AS PROTEIN TARGETING AGENTS

STATEMENT OF GOVERNMENT INTEREST

This invention was made with government support under Grant No. CA119347 and Grant No. CA151819 awarded by the National Institutes of Health and under Grant No. W911NF-09-D-0001 awarded by the U.S. Army Research Office. The government has certain rights in the invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 481274_401_SEQUENCE_LISTING.txt. The text file is 10.8 KB, was created on Jun. 19, 2014, and is being submitted electronically via EFS-Web.

BACKGROUND

Field

The present invention is generally directed to novel cyclic peptides and methods for their preparation and use as protein targeting agents.

Description of the Related Art

Detection of disease at the earliest stages requires multiplex measurements of key protein biomarkers in biological samples. The availability of high-affinity, highly selective compositions that recognize biomarkers from complex biological mixtures is a critical component for accurate detection of proteins that may indicate disease or changes in health. Peptide affinity agents have been suggested for use as agents for in vitro and/or in vivo detection of disease causing proteins.

Peptide affinity agents that bind to various targets (e.g. proteins) may be identified by screening large peptide libraries, and then using various techniques to identify which peptide library elements exhibit the desired interaction with the target. Those peptide libraries may be biologically synthesized (e.g. bacterial or viral phage display), or they may be chemically synthesized (e.g. one-bead-one-compound (OBOC) libraries). For chemically synthesized libraries, a candidate peptide binder is often first identified using a chemical label. For example, if a protein binds to a particular peptide sequence on a particular bead, then labeling that protein with a fluorescent molecule, or using a similarly labeled antibody to detect the bead-bound protein, can be used to identify the bead that contains the peptide of interest.

Regardless of their preparation method, the sequence of the peptide of interest must then be determined. Typical methods for determining that sequence include mass spectrometric sequencing, or Edman degradation. Thus, peptide libraries for identification of protein affinity agents are preferably readily sequencable by common techniques.

Accordingly, while progress has been made in this field, there remains a need in the art for improved protein targeting peptides. In particular, there is a need for readily sequencable cyclic peptides useful as protein targeting agents and methods for identifying the same. The present invention fulfills this need and provides further related advantages.

BRIEF SUMMARY OF THE INVENTION

In brief, the present invention is directed to cyclic peptides having activity as protein affinity agents, including stereoisomers, pharmaceutically acceptable salts and prodrugs thereof, and methods for identification and use of the same. Advantageously, embodiments of the cyclic peptides described herein can be prepared from natural and/or non-natural amino acids using common solid-state peptide synthesis techniques and can be readily sequenced. In various embodiments, the cyclic peptides comprise a variable region (VR) and constant region (CR). The variable region generally comprises a peptide sequence which varies among peptides in a library, thus providing a means for identifying a sequence having affinity for a desired target, such as a protein epitope. The constant region, in various embodiments, comprises functionality to aid in the screening process, such as: chemical groups that aid in sequencing, chemical groups that provide handles for various assays, chemical groups that are important for closing the peptide into a cycle (e.g., triazole, carbon-carbon double bonds), chemical groups that provide additional biochemical or chemical properties (stability, cell wall penetration, etc.) reporter groups (e.g., bimolecular labels such as biotin) and/or other useful chemical moieties. In certain embodiments, the CR comprises an exocyclic amine group which provides a means for sequencing the peptides via standard Edman degradation.

Accordingly, in one embodiment, a cyclic peptide having the following structure (I) is provided:

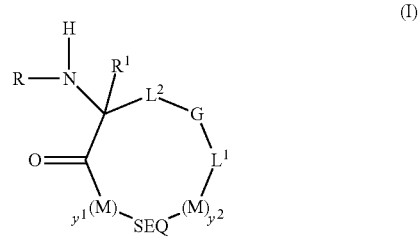

or a salt, tautomer, prodrug or stereoisomer thereof, wherein R, $R^1$, $L^1$, $L^2$, G, M, $Y^1$ $Y^2$ and SEQ are as defined herein. Compositions comprising the cyclic peptide structure (I) and libraries comprising a plurality of the cyclic peptides are also provided in other embodiments.

In another embodiment, a method for identifying a target binding agent compound is also provided, the method comprising:

A) providing a first peptide library comprising a plurality of first peptide library members, the first peptide library members optionally comprising an alkyne, azide or reporter moiety or combinations thereof;

B) contacting the first peptide library with a target or a truncated analogue thereof, the target or truncated analogue thereof comprising a first binding site and optionally an alkyne, azide or reporter moiety or combinations thereof;

C) identifying a first peptide library member with affinity for the first binding site and optionally modifying the first peptide library member to include an alkyne or azide moiety;

and optionally:

D) providing a second peptide library comprising a plurality of second peptide library members, the second peptide library members comprising an azide or alkyne or both;

E) contacting the second peptide library with a composition comprising the target or truncated analogue thereof and the first peptide library member of step C;

F) forming a triazole-linked conjugate between the first peptide library member of step C and a second peptide library member, the second peptide library member having affinity for a second binding site on the target or truncated analogue thereof, wherein the first peptide library, the second peptide library, or both, comprise cyclic peptides comprising:
  i. a sequence region comprising amino and carboxy termini and a variable peptide sequence of two to twenty amino acids selected from natural and non-natural amino acids; and
  ii. a linker region comprising a α-amino carbonyl, α-amido carbonyl, a methionine amino acid, or combinations thereof, and optionally comprising an alkyne, an azide, a linkage to a solid support or a linkage to a reporter moiety or a combination thereof, the linker region covalently linking the amino and carboxy termini of the sequence region.

In various other embodiments, uses of the cyclic peptides and methods employing the same are provided.

These and other aspects of the invention will be apparent upon reference to the following detailed description.

BRIEF DESCRIPTION OF THE SEVERAL VIEWS OF THE DRAWINGS

In the drawings, the sizes and relative positions of elements in the drawings are not necessarily drawn to scale. For example, the various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been selected solely for ease of recognition in the drawings.

FIG. 4 shows a generic structure for three cyclic peptide libraries and infrared data for a species within one of these libraries.

FIG. 7 shows the sequence of Akt2 with the targeted epitope in bold. Structures of two exemplary biligands and binding data for the same, relative to mono ligand, are also provided.

FIG. 8 provides the sequence for pLDH variants. The targeted eptiopes are highlighted.

FIG. 12 shows the structure and binding data for an exemplary biligand pfLDH binding agent. The illustrated biligand comprises a linear primary ligand and a cyclic secondary ligand.

DETAILED DESCRIPTION

Figure 1:
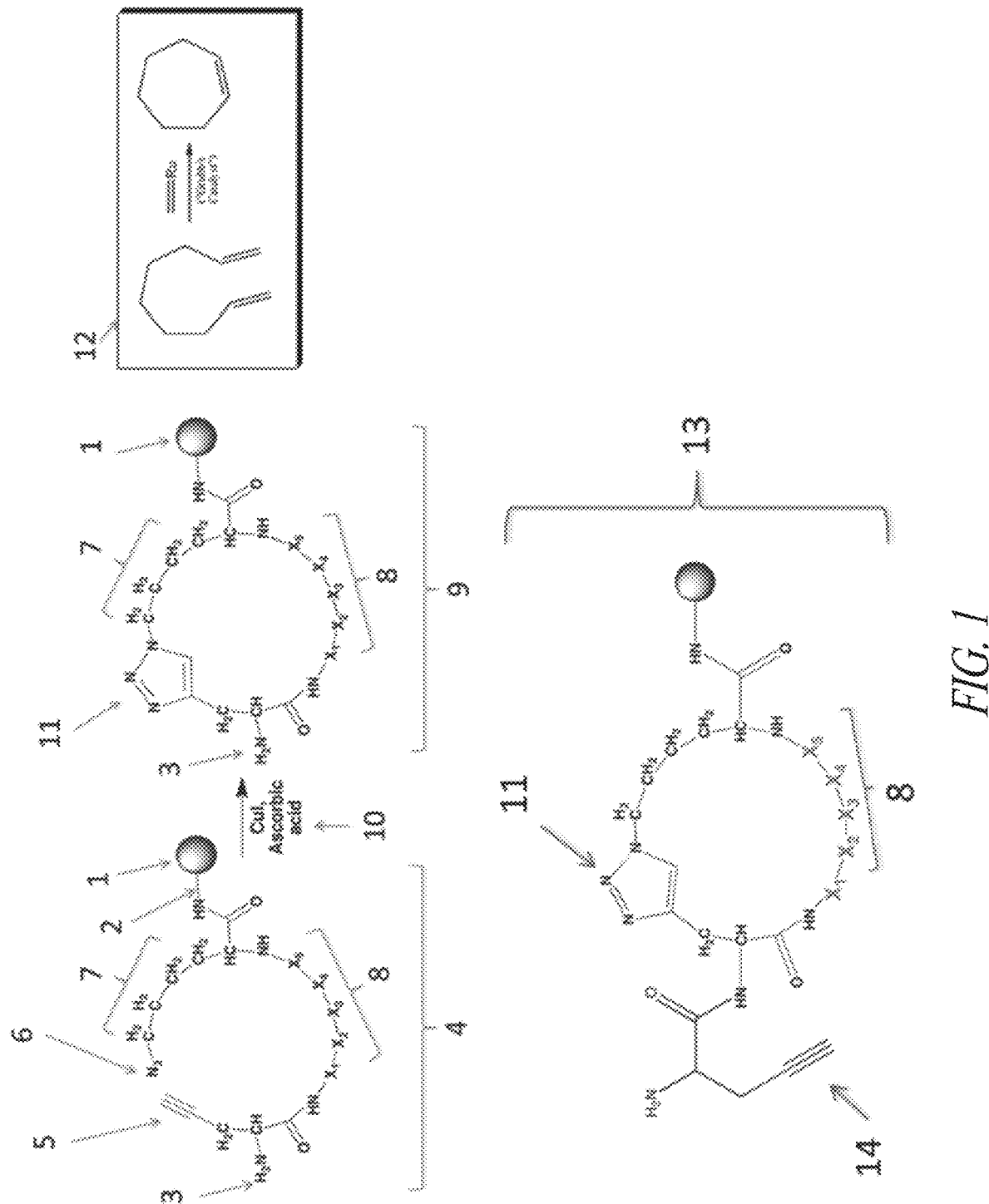
FIG. 1 illustrates cyclization of peptide libraries.

In the following description, certain specific details are set forth in order to provide a thorough understanding of various embodiments of the invention. However, one skilled in the art will understand that the invention may be practiced without these details.

Unless the context requires otherwise, throughout the present specification and claims, the word "comprise" and variations thereof, such as, "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Amino" refers to the —$NH_2$ radical.
"Cyano" refers to the —CN radical.
"Hydroxy" or "hydroxyl" refers to the —OH radical.
"Imino" refers to the =NH substituent.
"Nitro" refers to the —$NO_2$ radical.
"Oxo" refers to the =O substituent.
"Thioxo" refers to the =S substituent.

"Alkyl" refers to a straight or branched hydrocarbon chain radical consisting solely of carbon and hydrogen atoms, which is saturated or unsaturated (i.e., contains one or more double and/or triple bonds), having from one to twelve carbon atoms ($C_1$-$C_{12}$ alkyl), preferably one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Unless stated otherwise specifically in the specification, an alkyl group may be optionally substituted.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain may be optionally substituted.

"Alkoxy" refers to a radical of the formula —OR$_a$ where R$_a$ is an alkyl radical as defined above containing one to twelve carbon atoms. Unless stated otherwise specifically in the specification, an alkoxy group may be optionally substituted.

"Aminocarbonyl" refers to a radical of the formula —C(=O)NR$_a$R$_a$, where each R$_a$ is independently H, alkyl or a linker moiety.

"α-amino carbonyl" refers to a radical of the formula —C(=O)CR$_b$(NR$_a$R$_a$)—, where each R$_a$ is independently H, alkyl or a linker moiety and R$_b$ is H or alkyl. In some embodiments, an alpha amino carbonyl is part of a cyclic moiety (e.g., peptide) where the carbonyl is within the ring and the amino (NR$^a$R$^a$) is exocyclic. For example, in certain embodiments and alpha aminocarbonyl is useful for Edman degradation of cyclic peptides.

"α-amido carbonyl" refers to a radical of the formula —C(=O)CR$_b$(N(C=O)R$_a$R$_a$)—, where each R$_a$ is independently H, alkyl or a linker moiety and R$_b$ is H or alkyl. In some embodiments, an alpha amido carbonyl is part of a cyclic moiety (e.g., peptide) where the carbonyl is within the ring and the amido (N(C=O)R$^a$R$^a$) is exocyclic.

"Alkylamino" refers to a radical of the formula —NHR$_a$ or —NR$_a$R$_a$ where each R$_a$ is, independently, an alkyl radical as defined above containing one to twelve carbon atoms. Unless stated otherwise specifically in the specification, an alkylamino group may be optionally substituted.

"Thioalkyl" refers to a radical of the formula —SR$_a$ where R$_a$ is an alkyl radical as defined above containing one to twelve carbon atoms. Unless stated otherwise specifically in the specification, a thioalkyl group may be optionally substituted.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —R$_b$—R$_c$ where R$_b$ is an alkylene chain as defined above and R$_c$ is one or more aryl radicals as defined above, for example, benzyl, diphenylmethyl and the like. Unless stated otherwise specifically in the specification, an aralkyl group may be optionally substituted.

"Cycloalkyl" or "carbocyclic ring" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like. Unless otherwise stated specifically in the specification, a cycloalkyl group may be optionally substituted.

"Cycloalkylalkyl" refers to a radical of the formula —R$_b$R$_d$ where R$_b$ is an alkylene chain as defined above and R$_d$ is a cycloalkyl radical as defined above. Unless stated otherwise specifically in the specification, a cycloalkylalkyl group may be optionally substituted.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Heterocyclyl" or "heterocyclic ring" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, Unless stated otherwise specifically in the specification, a heterocyclyl group may be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group may be optionally substituted.

"Heterocyclylalkyl" refers to a radical of the formula —R$_b$R$_e$ where R$_b$ is an alkylene chain as defined above and R$_e$ is a heterocyclyl radical as defined above, and if the heterocyclyl is a nitrogen-containing heterocyclyl, the heterocyclyl may be attached to the alkyl radical at the nitrogen atom. Unless stated otherwise specifically in the specification, a heterocyclylalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group may be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group may be optionally substituted.

"Heteroarylalkyl" refers to a radical of the formula —$R_b R_f$ where $R_b$ is an alkylene chain as defined above and $R_f$ is a heteroaryl radical as defined above. Unless stated otherwise specifically in the specification, a heteroarylalkyl group may be optionally substituted.

The term "substituted" used herein means any of the above groups (e.g., alkyl, alkylene, alkoxy, alkylamino, aminocarbonyl, α-aminocarbonyl, α-amidocarbonyl, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_g R_h$, —$NR_g C(=O)R_h$, —$NR_g C(=O)NR_g R_h$, —$NR_g C(=O)OR_h$, —$NR_g SO_2 R_h$, —$OC(=O)NR_g R_h$, —$OR_g$, —$SR_g$, —$SOR_g$, —$SO_2 R_g$, —$OSO_2 R_g$, —$SO_2 OR_g$, =$NSO_2 R_g$, and —$SO_2 NR_g R_h$. "Substituted also means any of the above groups in which one or more hydrogen atoms are replaced with —$C(=O)R_g$, —$C(=O)OR_g$, —$C(=O)NR_g R_h$, —$CH_2 SO_2 R_g$, —$CH_2 SO_2 NR_g R_h$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

"Prodrug" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical Association and Pergamon Press, 1987.

The term "prodrug" is also meant to include any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of the invention and the like.

The invention disclosed herein is also meant to encompass all pharmaceutically acceptable peptides of structure (I) or (I') being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabelled compounds could be useful to help determine or measure the effectiveness of the compounds, by characterizing, for example, the site or mode of action, or binding affinity to pharmacologically important site of action. Certain isotopically-labelled peptides of the invention, for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled peptides can generally be prepared by conventional techniques known to those skilled in the art or by processes analogous to those described in the Preparations and Examples as set out below using an appropriate isotopically-labeled reagent in place of the non-labeled reagent previously employed.

The invention disclosed herein is also meant to encompass the in vivo metabolic products of the disclosed peptides. Such products may result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

"Mammal" includes humans and both domestic animals such as laboratory animals and household pets (e.g., cats, dogs, swine, cattle, sheep, goats, horses, rabbits), and non-domestic animals such as wildlife and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Effective amount" or "therapeutically effective amount" refers to that amount of a peptide of the invention which, when administered to a mammal, preferably a human, is sufficient to effect treatment of a disease or condition in the mammal, preferably a human. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition, i.e., relieving pain without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds (peptides) of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

The term "capture agent" as used herein refers to a protein-catalyzed capture (PCC) agent that comprises one or more target-binding moieties and which specifically binds to a target protein via those target-binding moieties. Each target-binding moiety exhibits binding affinity for the target protein, either individually or in combination with other target-binding moieties. In certain embodiments, each target-binding moiety binds to the target protein via one or more non-covalent interactions, including for example hydrogen bonds, hydrophobic interactions, and van der Waals interactions. A capture agent may comprise one or more organic molecules, including for example polypeptides, peptides, polynucleotides, and other non-polymeric molecules.

The terms "polypeptide," "peptide," and "protein" are used interchangeably herein to refer to an amino acid sequence comprising a polymer of amino acid residues. The terms apply to amino acid polymers in which one or more amino acid residues is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids, and isomers thereof. Naturally occurring amino acids are those encoded by the genetic code, as well as those amino acids that are later modified, e.g., hydroxyproline, carboxyglutamate, O-phosphoserine, and isomers thereof. The term "amino acid analogs" refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. The term "amino acid mimetics" refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission.

The term "non-natural amino acid" as used herein refers to an amino acid that is different from the twenty naturally occurring amino acids (alanine, arginine, glycine, asparagine, aspartic acid, cysteine, glutamine, glutamic acid, serine, threonine, histidine, lysine, methionine, proline, valine, isoleucine, leucine, tyrosine, tryptophan, phenylalanine) in its side chain functionality. The non-natural amino acid can be a close analog of one of the twenty natural amino acids, or it can introduce a completely new functionality and chemistry, as long as the hydrophobicity of the non-natural amino acid is either equivalent to or greater than that of the natural amino acid. The non-natural amino acid can either replace an existing amino acid in a protein (substitution), or be an addition to the wild type sequence (insertion). The incorporation of non-natural amino acids can be accomplished by known chemical methods including solid-phase peptide synthesis or native chemical ligation, or by biological methods.

The terms "specific binding," "selective binding," "selectively binds," or "specifically binds" as used herein refer to non-random binding of a binding agent (target binding compound) such as a capture agent to an epitope on a predetermined antigen. Binding agents (e.g., peptides) which specifically bind to a target are also referred to as having affinity for the target, or a binding site thereon. Typically, the binding agent binds with an affinity (KD) of approximately less than $10^{-7}$ M, such as approximately less than $10^{-8}$ M, $10^{-9}$ M or $10^{-10}$ M or even lower.

The term "KD" as used herein refers to the dissociation equilibrium constant of a particular interaction between a binding agent such as a capture agent and its antigen. Typically, the binding agents of the invention bind to a target (e.g., AKT) with a dissociation equilibrium constant (KD) of less than approximately $10^{-7}$ M, such as less than approximately $10^{-8}$ M, $10^{-9}$ M or $10^{-10}$ M or even lower, for example, as determined using surface plasmon resonance (SPR) technology in a Biacore instrument using the antigen as the ligand and the capture agent as the analyte, and binds to the predetermined antigen with an affinity corresponding to a KD that is at least ten-fold lower, such as at least 100 fold lower, for instance at least 1,000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the KD of the capture agent, so that when the KD of the capture agent very low (that is, the capture agent is highly specific), then the amount with which the affinity for the antigen is lower than the affinity for a non-specific antigen may be at least 10,000 fold.

The term "kd" (sec') as used herein refers to the dissociation rate constant of a particular binding agent-antigen interaction. Said value is also referred to as the koff value.

The term "ka" (M-'xsec') as used herein refers to the association rate constant of a particular binding agent-antigen interaction.

The term "KD" (M) as used herein refers to the dissociation equilibrium constant of a particular binding agent-antigen interaction.

The term "KA" (M-') as used herein refers to the association equilibrium constant of a particular binding agent-antigen interaction and is obtained by dividing the ka by the kd.

The term "condition" as used herein refers generally to a disease, event, or a change in health status. A change in health status may be associated with a particular disease or event, in which case the change may occur simultaneously with or in advance of the disease or event. In those cases where the change in health status occurs in advance of a disease or event, the change in health status may serve as a predictor of the disease or event. For example, a change in health status may be an alteration in the expression level of a particular gene associated with a disease or event. Alternatively, a change in health status may not be associated with a particular disease or event.

"Akt" refers to any of three isoforms of Akt (Akt1, Akt2, Akt3), a serine/threonine kinase also known in the art as Protein Kinase B. "Kinase" refers to a polypeptide or enzyme whose natural activity is to transfer phosphate groups from high-energy donor molecules such as ATP to specific substrates.

The term "antibody" as used herein refers to a protein of the kind that is produced by activated B cells after stimulation by an antigen and can bind specifically to the antigen promoting an immune response in biological systems. Full antibodies typically consist of four subunits including two heavy chains and two light chains. The term antibody includes natural and synthetic antibodies, including but not limited to monoclonal antibodies, polyclonal antibodies or fragments thereof. Exemplary antibodies include IgA, IgD, IgG1, IgG2, IgG3, IgM and the like. Exemplary fragments include Fab, Fv, Fab', F(ab')2 and the like. A monoclonal antibody is an antibody that specifically binds to and is thereby defined as complementary to a single particular spatial and polar organization of another biomolecule which is termed an "epitope." In some forms, monoclonal antibodies can also have the same structure. A polyclonal antibody refers to a mixture of different monoclonal antibodies. In some forms, polyclonal antibodies can be a mixture of monoclonal antibodies where at least two of the monoclonal antibodies binding to a different antigenic epitope. The different antigenic epitopes can be on the same target, different targets, or a combination. Antibodies can be prepared by techniques that are well known in the art, such as immunization of a host and collection of sera (polyclonal) or by preparing continuous hybridoma cell lines and collecting the secreted protein (monoclonal).

The term "stable" as used herein with regard to the disclosed peptides or pharmaceutical formulation thereof means that the agent or formulation maintains structural and functional integrity for a sufficient period of time to be useful in the methods described herein.

The term "synthetic" as used herein with regard to the disclosed peptides means that the capture agent has been generated by chemical rather than biological means.

Unless otherwise stated, sequence identity/similarity values provided herein refer to the value obtained using the BLAST 2.0 suite of programs using default parameters (Altschul, et al., (1997) Nucleic Acids Res. 25:3389-402).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) Comput. Chem. 17:149-63) and XNU (Claverie and States, (1993) Comput. Chem. 17:191-201) low-complexity filters can be employed alone or in combination.

As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) Computer Applic. Biol. Sci. 4:11-17, e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" or "substantially identical" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 55-100%, preferably at least 55%, preferably at least 60%, more preferably at least 70%, 80%, 90% and most preferably at least 95%.

Peptide Binding Agents

In situ click chemistry (J. Am. Chem. Soc. 126:12809 (2004); Angew. CHem. Int. Ed. Engl. 44:116 (2004); Angew. Chem. Int. Ed. Engl. 45:1435 (2006)) is a technique in which a small molecule enzymatic inhibitor is separated into two moieties, each of which is then expanded into a small library—one containing acetylene functionalities, and the other containing azide groups. The enzyme itself then assembles the 'best fit' inhibitor from these library components by selectively promoting 1,3-dipolar cycloaddition between the acetylene and azide groups to form a triazole linkage (the 'click' reaction). The enzyme promotes the click reaction only between those library components that bind to the protein in the right orientation. The resultant inhibitor can exhibit far superior affinity characteristics relative to the initial inhibitor that formed the basis of the two libraries (Proc. Natl. Acad. Sci. USA 97:9367 (1981); J. Comput. Aided. Mol. Des. 16:741 (2002)).

Sequential in situ click chemistry extends the in situ click chemistry concept to enable the discovery of multiligand capture agents. This process was used previously to produce a triligand capture agent against the model protein carbonic anhydrase II (CAII) (Angew. Chem. Int. Ed. Engl. 48:4944 (2009)). Sequential in situ click chemistry has several advantages. First, structural information about the protein target is replaced by the ability to sample a very large chemical space to identify the ligand components of the capture agent. For example, an initial ligand may be identified by screening the protein against a large (>$10^6$ element) one-bead-one-compound (OBOC) (Nature 354:83 (1991)) peptide library, where the peptides themselves may be comprised of natural, non-natural, and/or artificial amino acids. The resultant anchor ligand is then utilized in an in situ click screen, again using a large OBOC library, to identify a biligand binder. A second advantage is that the process can be repeated, so that the biligand is used as an anchor to identify a triligand, and so forth. The final capture agent can then be scaled up using relatively simple and largely automated chemistries, and it can be developed with a label, such as a biotin group, as an intrinsic part of its structure. This approach permits the exploration of branched, cyclic, and linear capture agent architectures. While many strategies for protein-directed multiligand assembly have been described (Science 274:1531 (1996); Proc. Natl. Acad. Sci. USA 97:9367 (2000)), most require detailed structural information on the target to guide the screening strategy, and most (such as the original in situ click approach), are optimized for low-diversity small molecule libraries.

The binding agents of certain embodiments of the present invention can be better understood by reference to the figures. FIG. 1 depicts an exemplary embodiment of the disclosed cyclic peptides and formation thereof. The peptide (and libraries thereof) is synthesized using a bead 1 or related solid support. A linker 2 connects the peptide to the bead, and can impart additional properties such as a site for peptide cleavage. The depicted peptide also contains a free amine 3 which is useful for sequencing by Edman degradation. Prior to closing, the open peptide 4 contains an acetylene 5 and an azide 6 group, plus a constant region (CR) 7 and a variable region (VR) 8. The cyclized peptide 9 has been closed using Cu catalyzed click chemistry to form a triazole 10.

An alternative for cyclizing the peptide library is to include carbon-carbon double bonds in the uncyclized peptide and use the ring closing metathesis reaction 12. For this approach, all other aspects of the peptide library may be retained, including the support 1, the variable region 8, the free amine 3, and other features.

Referring again to FIG. 1, 13 illustrates a cyclic peptide that presents an acetylene group 14 for the purposes of an in situ click reaction, for example with a second peptide ligand during formation of a bi-ligand binding agent. The acetylene group could also be an azide group, depending upon the in situ click reaction partner. For the preparation of this embodiment, the free amine 3 on 9 provides a point for attaching Boc-L-propargylglycine. Other means for preparation of such peptides are known or derivable by those of skill in the art.

Figure 2:
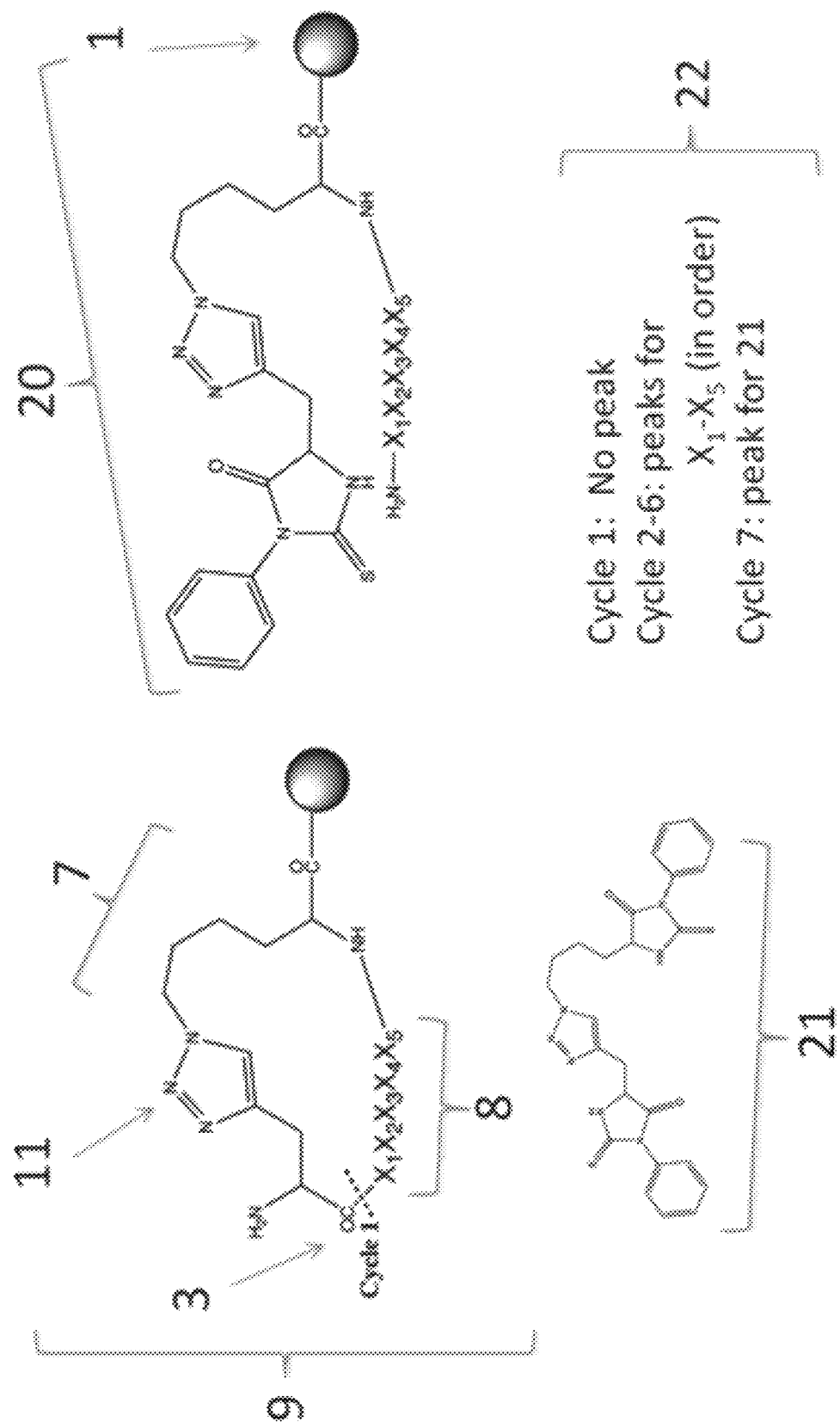
FIG. 2 shows sequencing of cyclic peptide libraries by Edman degradation.

Advantageously, the cyclic peptides of the invention are readily sequencable, and thus libraries of the same can be efficiently screened against a desired target. FIG. 2 illustrates one exemplary embodiment for sequencing the peptides using Edman degradation chemistry. As shown in FIG. 2, the exemplified cyclic peptide 9 contains a free amine site 3 that is initially cleaved, using an Edman degradation chemical cycle, to open the ring to form 20. The order of how the cyclic peptide is sequenced is provided in 22. Nothing is released from the cyclic peptide during the ring opening step. Subsequent cycles release, in order, the peptides that comprise the variable region 8, followed by the cleaved molecule 21 that contains the triazole 11 and the constant region 7.

Figure 3:
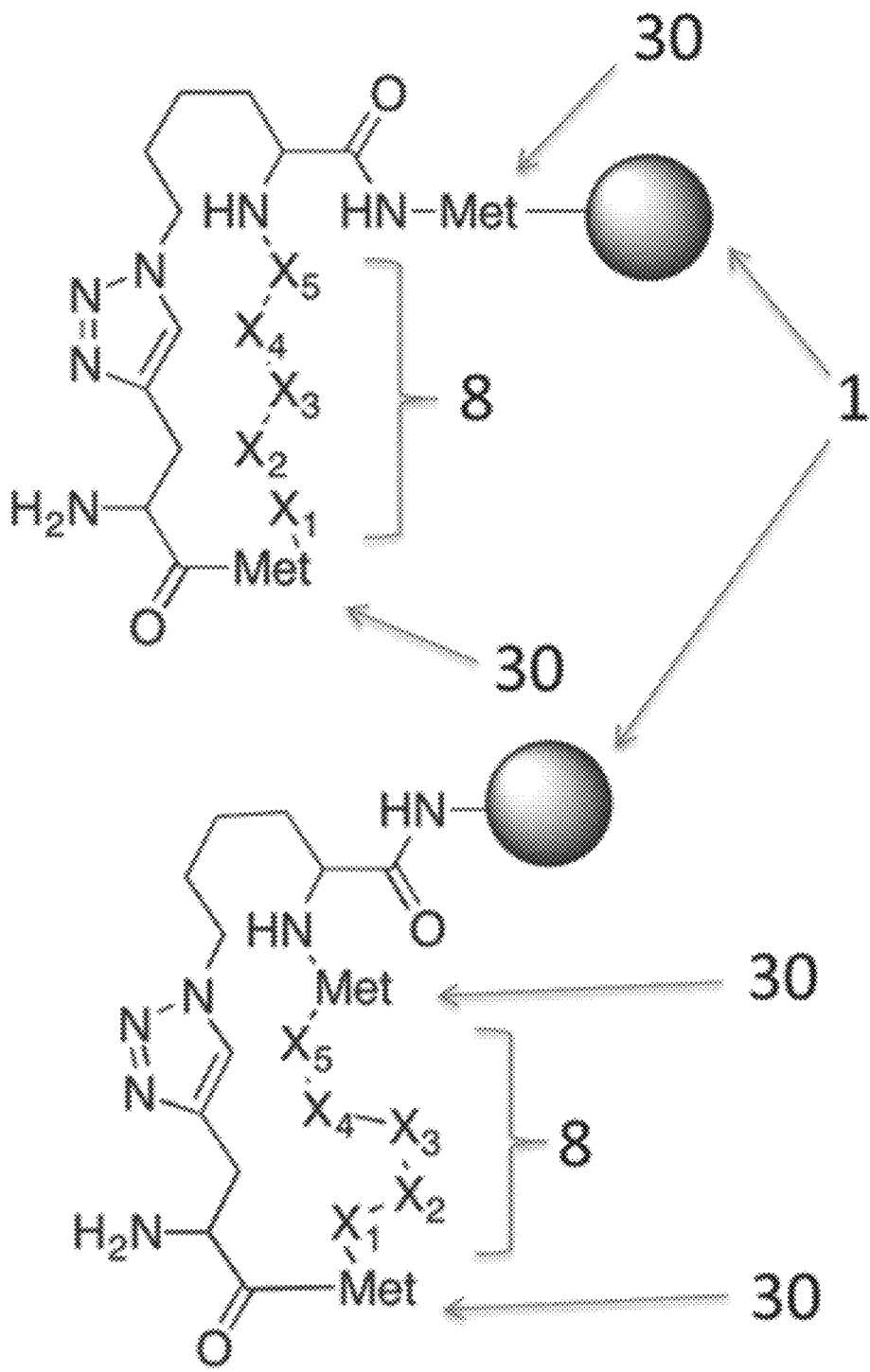
FIG. 3 presents an exemplary embodiment for sequencing cyclic peptide libraries by mass spectrometry.

In other embodiments, the cyclic peptides are sequenced by mass spectrometric sequencing. One such exemplary embodiment is illustrated in FIG. 3. For mass spectrometric sequencing, the peptide is released as a unit from the support 1 by cleavage of strategically placed methionine amino acids 30, and fragmentation of the peptide within the mass spectrometer is utilized to identify the amino acid sequence, according to well-established protocols. Cyanobromide (CNBr) is used to cleave the cyclic peptide at the Met sites, thus releasing the peptide variable region, or the peptide variable region+constant region from the bead for subsequent sequencing. In both cases, CNBr treatment opens the cycle.

Accordingly, in one embodiment the invention provides a cyclic peptide having the following structure (I):

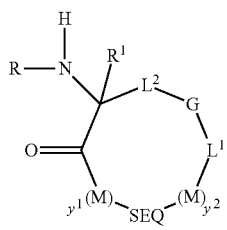

(I)

or a salt, tautomer, prodrug or stereoisomer thereof, wherein:

$L^1$ and $L^2$ are each individually optionally substituted linker moieties, each linker moiety optionally comprising a linkage to a solid support, a linkage to a reporter moiety, a linkage to a peptide ligand, a linkage to an alkyne or azide moiety or combinations thereof;

G is a triazole, a carbon-carbon double bond or an amide;

M is methionine;

R is H, -$L^3$-A or —C(=O)-$L^3$-A, where $L^3$ is a linker moiety and A is an alkyne, azide or a bond to a peptide ligand;

$R^1$ is H or $C_1$-$C_6$alkyl;

$Y^1$ and $Y^2$ are each individually 0 or 1; and

SEQ is an amino acid sequence comprising from 2 to 20 amino acids selected from natural and non-natural amino acids.

In some embodiments, G is a triazole. Such triazoles may be derived by reaction of an alkyne and azide on a precursor acyclic peptide.

In other embodiments, G is a carbon-carbon double bond. In some embodiments, these peptides are obtained by reactions of two carbon-carbon double bonds (alkenes) present in an acyclic precursor. Such reactions can be carried out using Grubbs metathesis chemistry, which is well-known to those of skill in the art.

In various other embodiments, $L^1$, $L^2$, or both, comprise one or more substituents selected from alkyl, alkyne, azide and aminocarbonyl. In some other embodiments of any of the foregoing, $L^1$, $L^2$, or both, comprise a linkage selected from a linkage to a solid support, a linkage to a reporter moiety and a linkage to a peptide ligand. In some specific embodiments of the foregoing, $L^1$ and $L^2$ are alkylene.

In some other embodiments of the foregoing, the cyclic peptide has one of the following structures (Ia) or (Ib):

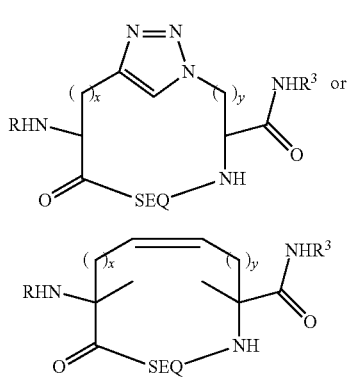

wherein:

$R^3$ is H, a linkage to a solid support, a linkage to a reporter moiety, a linkage to a peptide ligand, a linkage to an alkyne or azide moiety or combinations thereof; and x and y are each independently an integer from 1 to 8.

In some embodiments of the compounds of structure (Ia) and (Ib), x is 1. In other embodiments, x is 2. In more embodiments, x is 3. In still other embodiments, x is 4. In other embodiments, x is 5. In some other embodiments, x is 6. In yet more embodiments, x is 7. In other embodiments, x is 8.

In some embodiments of the compounds of structure (Ia) and (Ib), y is 1. In other embodiments, y is 2. In more embodiments, y is 3. In still other embodiments, y is 4. In other embodiments, y is 5. In some other embodiments, y is 6. In yet more embodiments, y is 7. In other embodiments, y is 8.

In other embodiments, R is H or —C(=O)-$L^3$-A, where $L^3$ is a linker moiety and A is a bond to a peptide ligand or an alkyne. In some of these embodiments, A is an alkyne. In other embodiments the cyclic peptide is biligand binding agent, and A is a bond to a peptide ligand, for example a linear peptide ligand or a cyclic peptide ligand. In further embodiments, the peptide ligand further comprises a second peptide ligand, and the cyclic peptide is this a tri-ligand binding agent.

The structure of the "linker moieties" (e.g., linker moieties to reporter moieties or further peptides, etc.) are not particularly limited. For example, in certain embodiments, linkers comprising ethylene glycol of various lengths (e.g., 1-10 glycol repeating units, e.g., about 5-7). Ethylene diamine linkers may also be employed alone or in combination with other moieties (e.g., ethylene glycol). Linker moieties comprising triazole (e.g., resulting from reaction of an alkyne and azide) are also useful in various embodiments.

In some of the foregoing embodiments, $y^1$ and $y^2$ are each 0.

In even more embodiments, the cyclic peptide has one of the following structures:

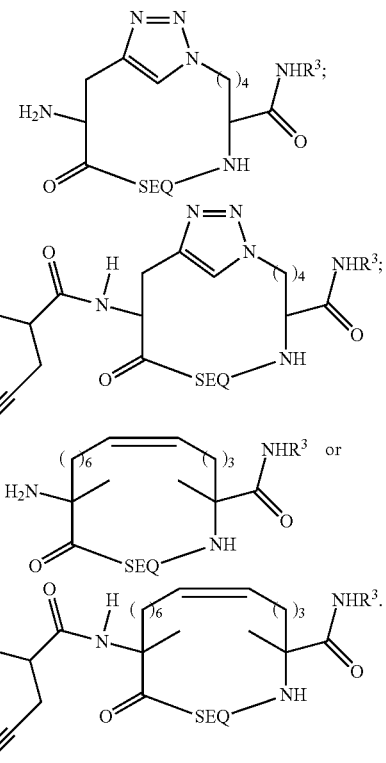

For example, in some of any of the foregoing embodiments SEQ comprises from 2 to 9 amino acids. In other embodiments, SEQ comprises from 5 to 7 amino acids.

In certain embodiments, SEQ comprise natural amino acids. In other embodiments, SEQ comprises non-natural amino acids. In still more embodiments, SEQ comprises natural and non-natural amino acids.

In some more specific embodiments any of the foregoing embodiments, the amino acids are selected from D and L stereoisomers of Ala, Gly, Leu, Ile, Val, Phe, Tip, Arg, His, Lys, Asp, Glu, Asn, Gln, Ser, Thr, Tyr and Pro.

The amino acids in SEQ are selected to have affinity for the desired target, including allosteric binding sites such as protein epitopes. In certain embodiments of the foregoing, SEQ has specific affinity for a binding region on Akt (e.g., Akt2), pfLDH, pvLDH, pfHRP(II) or HIV-1 p24.

In various other embodiments any of the foregoing embodiments, SEQ has 90% sequence identity to any one of SEQ ID NOS: 1-33. In other embodiments, SEQ has 95% sequence identity to any one of SEQ ID NOS: 1-33. In still other embodiments, SEQ has substantial identity to SEQ ID NOS: 1-33.

In still more other embodiments any of the foregoing embodiments, SEQ has one of the following sequences: YVYKS (SEQ ID NO: 1); VFAKV (SEQ ID NO: 2); IRYYS (SEQ ID NO: 3); YYTYT (SEQ ID NO: 4); RGGIL (SEQ ID NO: 5); KKIHL (SEQ ID NO: 6); ILYWK (SEQ ID NO: 7); PLKKG (SEQ ID NO: 8); LKTGQ (SEQ ID NO: 9); LKTGT (SEQ ID NO: 10); HWSAN (SEQ ID NO: 11); YWQW (SEQ ID NO:12); GHWSAN (SEQ ID NO: 13); YLGHK (SEQ ID NO: 14); LAYPP (SEQ ID NO: 15); LAYPA (SEQ ID NO: 16); LAYAA (SEQ ID NO: 17); LAYAP (SEQ ID NO: 18); ELYKY (SEQ ID NO: 19); GIFAVT (SEQ ID NO: 20); GIVGAP (SEQ ID NO: 21); GNWPAA (SEQ ID NO: 22); GFNVDL (SEQ ID NO: 23); GWNVDL (SEQ ID NO: 24); GSTEWL (SEQ ID NO: 25); GSQEWL (SEQ ID NO: 26); GTESVA (SEQ ID NO: 27); GQITIY (SEQ ID NO: 28); GQIQIY (SEQ ID NO: 29); GTITIY (SEQ ID NO: 30); GTIQIY (SEQ ID NO: 31); GTAVNA (SEQ ID NO: 32) or GQAVNA (SEQ ID NO: 33).

In certain embodiments SEQ is SEQ ID NO: 4. In other embodiments SEQ is SEQ ID NO: 11. In some different embodiments SEQ is SEQ ID NO: 14.

Compositions comprising any of the foregoing cyclic peptides and a pharmaceutically acceptable carrier are also provided in various embodiments. In other embodiments, a library comprising a plurality of the forgoing cyclic peptides is provided.

In certain embodiments, the cyclic peptides (also referred to herein as capture agents or binding agents) provided herein have a shelf-life of greater than six months, meaning that they are stable in storage for greater than six months. In certain of these embodiments, the capture agents have a shelf-life of one year or greater, two years or greater, or more than three years. In certain of these embodiments, the capture agents are stored as a lyophilized powder. In certain embodiments, the capture agents provided herein have a longer shelf-life than a biologic binding to the same target protein.

In certain embodiments, the capture agents provided herein are stable at temperatures ranging from about −80° C. to about 120° C. In certain of these embodiments, the capture agents are stable within a temperature range of −80° to −40° C.; −40° to −20° C.; −20° to 0° C.; 0° to 20° C.; 20° to 40° C.; 40° to 60° C.; 60° to 80° C.; and/or 80° to 120° C.

In certain embodiments, the capture agents provided herein are stable across a wider range of temperatures than a biologic binding to the same target protein, and/or remain stable at a specific temperature for a longer time period than a biologic binding to the same target protein.

In certain embodiments, the pH of a capture agent provided herein is in the range of about 3.0 to about 12.0. In certain of these embodiments, the pH of the capture agent is in the range of about 5.0 to about 9.0. The pH of a capture agent may be adjusted to a physiologically compatible range using methods known in the art. For example, in certain embodiments the pH of the capture agent may be adjusted to the range of about 6.5 to about 8.5.

In certain embodiments, the capture agents provided herein are stable in blood serum for more than 12 hours. In certain of these embodiments, the capture agents are stable in blood serum for more than 18 hours, more than 24 hours, more than 36 hours, more than 48 hours, or more than 96 hours. In certain embodiments, the capture agents provided herein are stable for a longer period of time in blood serum than a biologic binding to the same target protein.

In certain embodiments, the capture agents provided herein may comprise one or more detection labels (reporter group), including for example biotin, copper-1,4,7,10-tetraazacyclododecane-1,4,7,10-tetraaceticacid (copper-DOTA), desferrioxamine B (DFO), a ligand for radiolabeling with $^{68}$Ga, or other radiolabeled products that may include gamma emitters, proton emitters, positron emitters, tritium, or covered tags detectable by other methods (i.e., gadolinium) among others.

In certain embodiments, the capture agents provided herein comprise one or more detectable labels. In certain of these embodiments, the label is copper-DOTA. In other embodiments, the detectable label is selected from $^{64}$Cu DOTA, $^{68}$Ga DOTA, $^{18}$F, $^{64}$Cu, $^{68}$Ga, $^{89}$Zr, $^{124}$I, $^{86}$Y, $^{94m}$Tc, $^{110m}$In, $^{11}$C and $^{76}$Br. In other embodiments, the detectable label is selected from $^{123}$I, $^{131}$I, $^{67}$Ga, $^{111}$In and $^{99m}$Tc. In other embodiments, the label is a fluorescent label.

In some other embodiments, the cyclic peptide comprises a linkage to a reporter moiety, the reporter moiety selected from polyethylene glycol (PEG), biotin, thiol and fluorophores. For example, in some embodiments the fluorophores are selected from FAM, FITC, Cy5, TRITC, TAMRA.

Table 1 provides reporter moieties useful in various different applications of the cyclic peptides. Other useful reporter moieties can be derived by one of skill in the art.

TABLE 1

Reporter Moieties

| Application | Reporter |
| --- | --- |
| ELISA: microtiter plate | Biotin |
| ELISA: lateral flow test | Biotin |
| Immunoprecipitation (and other bead-based assays) | Biotin, thiol |
| Dot blot | Biotin |
| Cell-based assay | Biotin, fluorophore |
| IHC | Biotin, fluorophore |
| In vivo imaging: PET | Radioisotopes including $^{18}$F, $^{68}$Ga, $^{64}$Cu, $^{89}$Zr, $^{124}$I |
| In vivo imaging: SPECT | Radioisotopes including $^{111}$In, $^{90}$Y, $^{99m}$Tc |
| In vivo imaging: MR | Gd$^{3+}$ |

In certain embodiments, the capture agents provided herein may be modified to obtain a desired chemical or biological activity. Examples of desired chemical or biological activities include, without limitation, improved solubility, stability, bioavailability, detectability, or reactivity. Examples of specific modifications that may be introduced to a capture agent include, but are not limited to, cyclizing the capture agent through formation of a disulfide bond; modifying the capture agent with other functional groups or molecules. Similarly, a capture agent may be synthesized to bind to non-canonical or non-biological epitopes on proteins, thereby increasing their versatility. In certain embodiments, the capture agent may be modified by modifying the synthesis blocks of the target-binding moieties before the coupling reaction.

Provided herein in certain embodiments are pharmaceutical formulations comprising one or more of the capture agents provided herein. In certain embodiments, these pharmaceutical formulations comprise one or more pharmaceutically acceptable carriers, excipients, or diluents. These carriers, excipients, or diluents may be selected based on the intended use and/or route of administration of the formulation.

Provided herein in certain embodiments are kits comprising one or more of the capture agents disclosed herein. In certain embodiments, these kits may be used for identifying, detecting, quantifying, and/or separating proteins, such as Akt, pfLDH, pvLDH, pfHRP(II) or HIV-1 p24., and in certain of these embodiments the kits may be used in the diagnosis and/or staging of a condition associated with increased Akt, pfLDH, pvLDH, pfHRP(II) or HIV-1 p24 expression and/or activity. In certain embodiments, a kit as provided herein comprises: (a) a substrate comprising an adsorbent thereon, wherein the adsorbent is suitable for binding Akt, pfLDH, pvLDH, pfHRP(II) or HIV-1 p24, and (b) a washing solution or instructions for making a washing solution, wherein the combination of the adsorbent and the washing solution allows detection of Akt, pfLDH, pvLDH, pfHRP(II) or HIV-1 p24. In other embodiments, the kits provided herein may be used in the treatment of a condition associated with increased Akt or V Akt, pfLDH, pvLDH, pfHRP(II) or HIV-1 p24 expression and/or activity.

In certain embodiments, the kits provided herein may further comprise instructions for suitable operational parameters in the form of a label or a separate insert. For example, the kit may have standard instructions informing a consumer/kit user how to wash the probe after a sample of plasma or other tissue sample is contacted on the probe.

In certain embodiments, a kit as provided herein comprises (a) one or more Akt, pfLDH, pvLDH, pfHRP(II) or HIV-1 p24 capture agents that specifically bind Akt, pfLDH, pvLDH, pfHRP(II) or HIV-1 p24; and (b) a detection reagent. Such kits can be prepared from the materials described herein.

The kits provided herein may optionally comprise a standard or control information, and/or a control amount of material, so that the test sample can be compared with the control information standard and/or control amount to determine if the test amount of Akt, pfLDH, pvLDH, pfHRP(II) or HIV-1 p24 detected in a sample is an amount consistent with a diagnosis of a particular condition.

It is understood that any embodiment of the peptides, as set forth above, and any specific substituent set forth herein for a R, $R^1$, $L^1$, $L^2$, G, M, $Y^1$ $Y^2$ or SEQ group in the peptides, as set forth above, may be independently combined with other embodiments and/or substituents of the peptides to form embodiments of the inventions not specifically set forth above. In addition, in the event that a list of substituents is listed for any particular variable in a particular embodiment and/or claim, it is understood that each individual substituent may be deleted from the particular embodiment and/or claim and that the remaining list of substituents will be considered to be within the scope of the invention.

For the purposes of administration, the peptides of the present invention may be administered as a raw chemical or may be formulated as pharmaceutical compositions. Pharmaceutical compositions of the present invention comprise a peptide of structure (I) and a pharmaceutically acceptable carrier, diluent or excipient. The peptide of structure (I) is present in the composition in an amount which is effective to treat a particular disease or condition of interest—that is, and preferably with acceptable toxicity to the patient. Activity of compounds of the peptides can be determined by one skilled in the art, for example, as described in the Examples. Appropriate concentrations and dosages can be readily determined by one skilled in the art.

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see *Remington: The Science and Practice of Pharmacy,* 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

Compounds of the invention, or pharmaceutically acceptable derivatives thereof, may also be administered simultaneously with, prior to, or after administration of one or more other therapeutic agents. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and the other active agent can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

It is understood that in the present description, combinations of substituents and/or variables of the depicted formulae are permissible only if such contributions result in stable compounds.

It will also be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

Furthermore, all compounds of the invention which exist in free base or acid form can be converted to their pharmaceutically acceptable salts by treatment with the appropriate inorganic or organic base or acid by methods known to one skilled in the art. Salts of the compounds of the invention can be converted to their free base or acid form by standard techniques.

The peptides of the invention can be prepared by procedures known to those of skill in the art. For example, the peptides can be prepared using standard solid-phase peptide synthesis techniques, and modifications thereof. Modified amino acids may be employed to incorporate amino acids comprising alkyne and/or azide moieties and/or alkene moieties useful for cyclization. Methods for cyclizing the peptides using azide/alkyne chemistry and Grubbs metathesis chemistry are well-known in the art. Such methods are described in more detail in the examples.

It is understood that one skilled in the art may be able to make these compounds by similar methods or by combining other methods known to one skilled in the art. It is also understood that one skilled in the art would be able to make, in a similar manner as described below, other peptides not specifically illustrated in the examples below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described in this invention.

Methods for Use of the Peptides

In various embodiments, the present invention provides methods for identification of cyclic peptides which are useful as binding agents for various targets. In general, the methods employ cyclic peptides, such as any of the cyclic peptides described herein above, in methods for identification of mono-, bi- and/or tri-ligand binding agents. Higher order binding agents (tetra, penta, and the like) are also within the scope of the present invention.

In general, the present invention includes any methods employing the cyclic peptides described herein. Accordingly, in one embodiment a method for identifying a target binding compound (e.g., a protein capture agent) is provided, the method comprising A). providing a peptide library comprising a plurality of cyclic peptides comprising:
  i. a sequence region comprising amino and carboxy termini and a variable peptide sequence of two to twenty amino acids selected from natural and non-natural amino acids; and
  ii. a linker region comprising a α-amino carbonyl, α-amido carbonyl, a methionine amino acid, or combinations thereof, and optionally comprising an alkyne, an azide, a linkage to a solid support or a linkage to a reporter moiety or a combination thereof, the linker region covalently linking the amino and carboxy termini of the sequence region.

B) contacting the peptide library with a target or a truncated analogue thereof, the target or truncated analogue thereof comprising a binding site and optionally an alkyne, azide or reporter moiety or combinations thereof;

C) identifying a peptide library member with affinity for the binding site

In further embodiments, a method for identifying a target binding compound (e.g., a protein capture agent) is provided, the method comprising:

A) providing a first peptide library comprising a plurality of first peptide library members, the first peptide library members optionally comprising an alkyne, azide or reporter moiety or combinations thereof;

B) contacting the first peptide library with a target or a truncated analogue thereof, the target or truncated analogue thereof comprising a first binding site and optionally an alkyne, azide or reporter moiety or combinations thereof;

C) identifying a first peptide library member with affinity for the first binding site and optionally modifying the first peptide library member to include an alkyne or azide moiety;

and optionally:

D) providing a second peptide library comprising a plurality of second peptide library members, the second peptide library members comprising an azide or alkyne or both;

E) contacting the second peptide library with a composition comprising the target or truncated analogue thereof and the first peptide library member of step C;

F) forming a triazole-linked conjugate between the first peptide library member of step C and a second peptide library member, the second peptide library member having affinity for a second binding site on the target or truncated analogue thereof, wherein the first peptide library, the second peptide library, or both, comprise cyclic peptides comprising:

i. a sequence region comprising amino and carboxy termini and a variable peptide sequence of two to twenty amino acids selected from natural and non-natural amino acids; and ii. a linker region comprising a α-amino carbonyl, α-amido carbonyl, a methionine amino acid, or combinations thereof, and optionally comprising an alkyne, an azide, a linkage to a solid support or a linkage to a reporter moiety or a combination thereof, the linker region covalently linking the amino and carboxy termini of the sequence region.

For purposes of clarity, it should be noted that steps D-F are optional and the above described method is not limited to methods which require conjugation of a second peptide. It is understood that when steps D-F are not performed, the first library comprises the cyclic peptide; however when steps D-F are performed the cyclic peptides may be a part of either the first, second or both libraries. It should also be emphasized that the methods are not limited to identification of mono or bi-ligand binding agents, and the methods described herein can be extrapolated to identification of tertiary, ternary and higher binding agents (e.g., by performing steps analogous to steps D-F). In general, any of the cyclic peptides described herein above may be employed in the above methods. Specific embodiments of the peptides useful in the some embodiments of the methods are illustrated herein.

In certain embodiments of the method, the linker region comprises a α-amino carbonyl group bound to the amino terminus of the peptide sequence. In some of these embodiments, the method further comprises determining the peptide sequence of one or more of the cyclic peptides by Edman degradation.

In other embodiments, the linker region comprises a methionine amino acid bound to the amino terminus of the variable peptide sequence. In some of these embodiments, the method further comprises treating one or more of the cyclic peptides with CNBr and determining the sequence thereof by mass spectrometry.

In other embodiments of the foregoing methods, the linker region comprises an alkyne or azide, the target or a truncated analogue thereof comprises an alkyne or azide and identifying the first peptide library member with affinity for the first binding site comprises identifying first peptide library members which form a triazole linkage with the target or a truncated analogue thereof.

In some embodiments, the first peptide library is contacted with a truncated analogue of the target.

In other aspects, the method further comprises modifying the triazole linked conjugate to contain a triazole or alkyne and contacting the modified conjugate with the target or truncated analogue thereof and a third peptide library, the third peptide library comprising a plurality of third peptide library members, each third peptide library member comprising an azide or alkyne.

In still other embodiments, the method further comprises forming a triazole linkage between the modified conjugate and a member of the third peptide library, the third peptide library member having affinity for a third binding site on the target or truncated analogue thereof.

In some embodiments, the first binding site is an epitope. In other embodiments, the second binding site is an epitope. In some more embodiments, the third binding site is an epitope.

In various different embodiments, the linker region comprises a carbon-carbon double bond or a triazole.

In some embodiments the cyclic peptides have the following structure (I'):

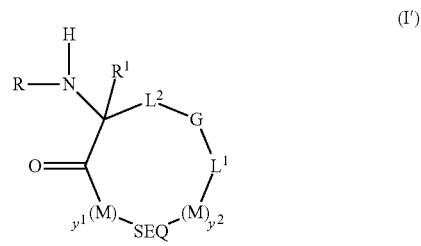

or a salt, tautomer or stereoisomer thereof, wherein:

$L^1$ and $L^2$ are each individually optionally substituted linker moieties, each linker moiety optionally comprising a linkage to a solid support, a linkage to a reporter moiety, a linkage to an alkyne or azide moiety or a linkage to a peptide ligand;

G is a triazole a carbon-carbon double bond or an amide;

M is methionine;

R is H, $-L^3$-A or $-C(=O)-L^3$-A, where $L^3$ is a linker moiety and A is an alkyne or azide;

$R^1$ is H or $C_1$-$C_6$alkyl;

$Y^1$ and $Y^2$ are each individually 0 or 1; and

SEQ is the variable peptide sequence.

In some embodiments, $Y^1$ and $Y^2$ are each 0.

For example, in some of any of the foregoing embodiments SEQ comprises from 2 to 9 amino acids. In other embodiments, SEQ comprises from 5 to 7 amino acids.

In certain embodiments, SEQ comprise natural amino acids. In other embodiments, SEQ comprises non-natural amino acids. In still more embodiments, SEQ comprises natural and non-natural amino acids.

In some more specific embodiments any of the foregoing embodiments, the amino acids are selected from D and L stereoisomers of Ala, Gly, Leu, Ile, Val, Phe, Trp, Arg, His, Lys, Asp, Glu, Asn, Gln, Ser, Thr, Tyr and Pro.

The amino acids in SEQ are selected to have affinity for the desired target, including allosteric binding sites such as protein epitopes. In certain embodiments of the foregoing, SEQ has specific affinity for a binding region on Akt (e.g., Akt2), pfLDH, pvLDH, pfHRP(II) or HIV-1 p24.

In various other embodiments any of the foregoing embodiments, SEQ has 90% sequence identity to any one of SEQ ID NOS: 1-33. In other embodiments, SEQ has 95% sequence identity to any one of SEQ ID NOS: 1-33. In still other embodiments, SEQ has substantial identity to SEQ ID NOS: 1-33.

In still more other embodiments any of the foregoing embodiments, SEQ has one of the following sequences: YVYKS (SEQ ID NO: 1); VFAKV (SEQ ID NO: 2); IRYYS (SEQ ID NO: 3); YYTYT (SEQ ID NO: 4); RGGIL (SEQ ID NO: 5); KKIHL (SEQ ID NO: 6); ILYWK (SEQ ID NO: 7); PLKKG (SEQ ID NO: 8); LKTGQ (SEQ ID NO: 9); LKTGT (SEQ ID NO: 10); HWSAN (SEQ ID NO: 11); YWQW (SEQ ID NO:12); GHWSAN (SEQ ID NO: 13); YLGHK (SEQ ID NO: 14); LAYPP (SEQ ID NO: 15); LAYPA (SEQ ID NO: 16); LAYAA (SEQ ID NO: 17); LAYAP (SEQ ID NO: 18); ELYKY (SEQ ID NO: 19); GIFAVT (SEQ ID NO: 20); GIVGAP (SEQ ID NO: 21); GNWPAA (SEQ ID NO: 22); GFNVDL (SEQ ID NO: 23); GWNVDL (SEQ ID NO: 24); GSTEWL (SEQ ID NO: 25); GSQEWL (SEQ ID NO: 26); GTESVA (SEQ ID NO: 27); GQITIY (SEQ ID NO: 28); GQIQIY (SEQ ID NO: 29);

GTITIY (SEQ ID NO: 30); GTIQIY (SEQ ID NO: 31); GTAVNA (SEQ ID NO: 32) or GQAVNA (SEQ ID NO: 33).

In certain embodiments SEQ is SEQ ID NO: 4. In other embodiments SEQ is SEQ ID NO: 11. In some different embodiments SEQ is SEQ ID NO: 14.

In other embodiments, the cyclic peptides have the following structure (I'a):

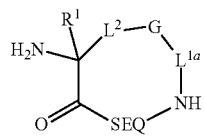
(I'a)

wherein:

$L^{1a}$ is a linker moiety optionally substituted with one or more substituent selected from a linkage to an alkyne or azide moiety, a linkage to a solid support and a linkage to a reporter moiety.

In some embodiments, $L^{1a}$ and $L^2$ are each independently optionally substituted alkylene.

In other embodiments, the cyclic peptides have the following structure (I'b):

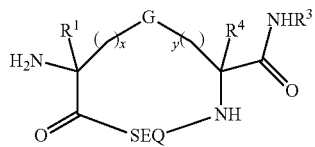
(I'b)

wherein:

$R^3$ is H, a linkage to a solid support, a linkage to an alkyne or azide moiety or a linkage to a reporter moiety;

$R^4$ is H or $C_1$-$C_6$alkyl; and x and y are each independently integers from 1 to 8.

In certain of the forgoing embodiments, G is a triazole. In other embodiments, G is a carbon-carbon double bond.

In some more specific embodiments, the cyclic peptides have one of the following structures:

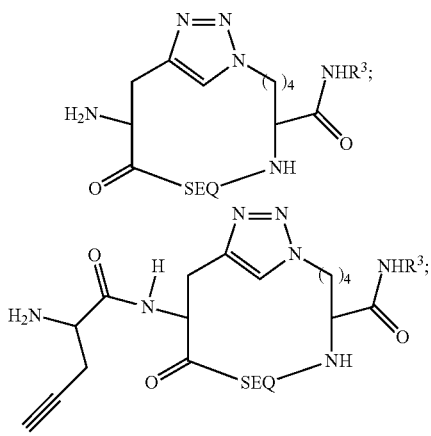

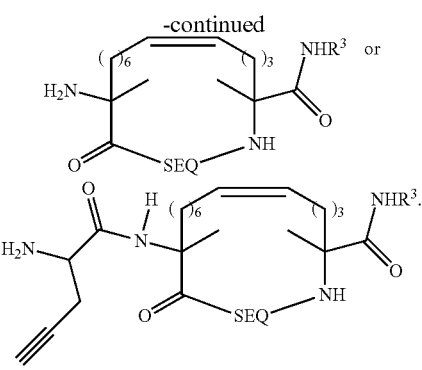

In still other embodiments, the first peptide library comprises the cyclic peptides, and the second peptide library comprises linear peptide members.

In different embodiments, the second peptide library comprises the cyclic peptides, and the first peptide library comprises linear peptide members.

In more embodiments, the first and second peptide library comprises the cyclic peptides.

In some embodiments, the target is a protein, for example a protein epitope. In some embodiments, the protein is an enzyme or cell surface protein. In other embodiments, the target is AkT2, pfLDH, pvLDH, pfHRP, or HIV-1 p24 antigen.

Provided herein in certain embodiments are methods of using the capture agents disclosed herein to identify, detect, quantify, and/or separate target proteins in a biological sample. In some embodiments the target protein are AKT (e.g., AKt2), pfLDH, pvLDH, pfHRP, or HIV-1 p24 antigen. The capture agents disclosed herein can serve as a drop-in replacement for monoclonal antibodies in biochemical assays. Therefore, in certain embodiments the methods provided herein utilize an immunoassay, with the capture agent replacing an antibody or its equivalent. In certain embodiments, the immunoassay may be a Western blot, pull-down assay, dot blot, or ELISA.

A biological sample for use in the methods provided herein may be selected from the group consisting of organs, tissue, bodily fluids, and cells. Where the biological sample is a bodily fluid, the fluid may be selected from the group consisting of blood, blood serum, plasma, urine, sputum, saliva, stool, spinal fluid, cerebral spinal fluid, lymph fluid, skin secretions, respiratory secretions, intestinal secretions, genitourinary tract secretions, tears, and milk.

Provided herein in certain embodiments are methods of identifying, detecting, quantifying, and/or localizing a target protein in vivo. In certain of these embodiments, the capture agents may be used as an imaging agent. In these embodiments, the capture agents may comprise one or more detection labels as discussed above.

Provided herein in certain embodiments are methods of using the capture agents disclosed herein to inhibit a target protein activity. In certain of these embodiments, the capture agents inhibit target protein activity by blocking binding of the target protein to its native substrate.

Provided herein in certain embodiments are methods of using the capture agents disclosed herein to diagnose and/or classify (e.g., stage) a condition associated with increased target protein expression and/or activity. In certain embodiments, these methods comprise (a) obtaining a biological sample from a subject; (b) measuring the presence or absence of target protein in the sample with the capture agent; (c) comparing the levels of target protein to a predetermined control range for target protein; and (d) diagnosing a condition associated with increased target protein expression based on the difference between target protein levels in the biological sample and the predetermined control.

In certain embodiments of the diagnosis and/or classification methods provided herein, the capture agents may be used to diagnose a change in health status in a subject, wherein the change in health status is a predictor of a disease or event. In certain of these embodiments, the methods may be utilized to predict the development of a disease or event in a subject who does not yet exhibit any symptoms of the disease or event. In certain embodiments, the change in health status may be an increase in target protein levels.

Provided herein in certain embodiments are methods of treating a condition associated with increased target protein expression and/or activity in a subject in need thereof by administering a therapeutically effective amount of one or more of the capture agents or pharmaceutical formulations disclosed herein. In certain of these embodiments, the capture agent(s) may be linked to one or more additional therapeutic agents, including for example a chemotherapeutic agent. In preferred embodiments, the capture agent is administered as a pharmaceutical composition.

A capture agent or pharmaceutical formulation may be administered to a patient in need of treatment via any suitable route. Routes of administration may include, for example, parenteral administration (including subcutaneous, intramuscular, intravenous, by means of, for example a drip patch). Further suitable routes of administration include (but are not limited to) oral, rectal, nasal, topical (including buccal and sublingual), infusion, vaginal, intradermal, intraperitoneally, intracranially, intrathecal and epidural administration or administration via oral or nasal inhalation, by means of, for example a nebulizer or inhaler, or by an implant.

A capture agent or pharmaceutical formulation may also be administered via microspheres, liposomes, other microparticulate delivery systems or sustained release formulations placed in certain tissues including blood. Suitable examples of sustained release carriers include semi-permeable polymer matrices in the form of shared articles, e.g., suppositories or microcapsules. Examples of the techniques and protocols mentioned above and other techniques and protocols which may be used in accordance with the invention can be found in Remington's Pharmaceutical Sciences, 18th edition, Gennaro, A. R., Lippincott Williams & Wilkins; 20th edition (Dec. 15, 2000) ISBN 0-912734-04-3 and Pharmaceutical Dosage Forms and Drug Delivery Systems; Ansel, N. C. et al. 7th Edition ISBN 0-683305-72-7, the entire disclosures of which are herein incorporated by reference.

Provided herein in certain embodiments is the use of the capture agents disclosed herein in the preparation of a medicament for treating a condition associated with increased target protein expression and/or activity.

In other more specific embodiments, the invention is directed to a method of detecting Akt in a sample, the method comprising replacing an antibody or its equivalent in a cell-based or an immunoassay with any of the foregoing cyclic peptides. In some embodiments, the immunoassay is a Western blot, a pull-down assay, a dot blot or an ELISA.

In other embodiments, a method for inhibiting activity of a protein in a subject is provided, the method comprising administering an effective amount of any of the foregoing cyclic peptides to a subject in need thereof. In some embodiments, the protein is Akt. For example, in some aspects the method is for treating a disease or condition associated with increased Akt expression, Akt activity or both. In some embodiments, the disease or condition is cancer.

Other embodiments are directed to a method of purifying a target, the method comprising immobilizing any of the foregoing cyclic peptides in a column based format, contacting the column with a matrix containing the target, washing the column, and eluting the target.

Methods for imaging are also provided. For example, in one embodiment the invention provides a method of imaging in vivo target expression, the method comprising:
  a) providing any of the foregoing cyclic peptides, wherein SEQ is a peptide sequence having affinity for a location on or near a target expressing site in a subject, and modifying the cyclic peptide to include a small-molecule positron-emission-tomography ligand (PET ligand);
  b) administering the cyclic peptide of step a) to the subject;
  c) measuring the positron emission from the PET ligand at a first time;
  d) measuring the positron emission from the PET ligand at a second time; and
  e) comparing the positron emission from the PET ligand at the first and second times.

In certain embodiments of the foregoing, the PET ligand comprises a moiety selected from $^{64}$Cu DOTA, $^{68}$Ga DOTA, $^{68}$Ga NOTA, $^{18}$F, $^{64}$Cu, $^{68}$Ga, $^{89}$Zr, $^{124}$I, $^{86}$Y, $^{94m}$Tc, $^{110m}$In, $^{11}$C and $^{76}$Br.

In other embodiments, the imaging method is a method of imaging in vivo target expression, the method comprising:
  a) providing any of the foregoing cyclic peptides, wherein SEQ is a peptide sequence having affinity for a location on or near a target expressing site in a subject, and modifying the cyclic peptide to include a small-molecule single-photon-emission-computed-tomography ligand (SPECT ligand);
  b) administering the cyclic peptide of step a) to the subject;
  c) measuring the photon emission from the SPECT ligand at a first time;
  d) measuring the photon emission from the SPECT ligand at a second time; and
  e) comparing the photon emission from the SPECT ligand at the first and second times.

In some embodiments of the foregoing, the SPECT ligand comprises a moiety selected from $^{111}$In DOTA, $^{90}$Y DOTA, $^{111}$In, $^{90}$Y and $^{99m}$Tc.

In other embodiments, a method of imaging in vivo target expression is provided, the method comprising:
  a) providing any of the foregoing cyclic peptides, wherein SEQ is a peptide sequence having affinity for a location on or near a target expressing site in a subject, and modifying the cyclic peptide to include a magnetic resonance ligand (MR ligand);
  b) administering the cyclic peptide of step a) to the subject;
  c) measuring the magnetic resonance from the MR ligand at a first time;
  d) measuring the magnetic resonance from the MR ligand at a second time; and
  e) comparing the magnetic resonance from the MR ligand at the first and second times.

In some embodiments, the MR ligand comprises $Gd^{3+}$.

In other embodiments of the foregoing methods, the cyclic peptide comprises a linkage to a reporter moiety, the reporter moiety selected from polyethylene glycol (PEG), biotin, thiol and fluorophores. For example, in some embodiments the fluorophores are selected from FAM, FITC, Cy5, TRITC, TAMRA.

The following examples are provided for purposes of illustration, not limitation.

EXAMPLES

Example 1

Synthesis of Ring Closing Metathesis (RCM) Catalyzed OBOC Peptide Libraries

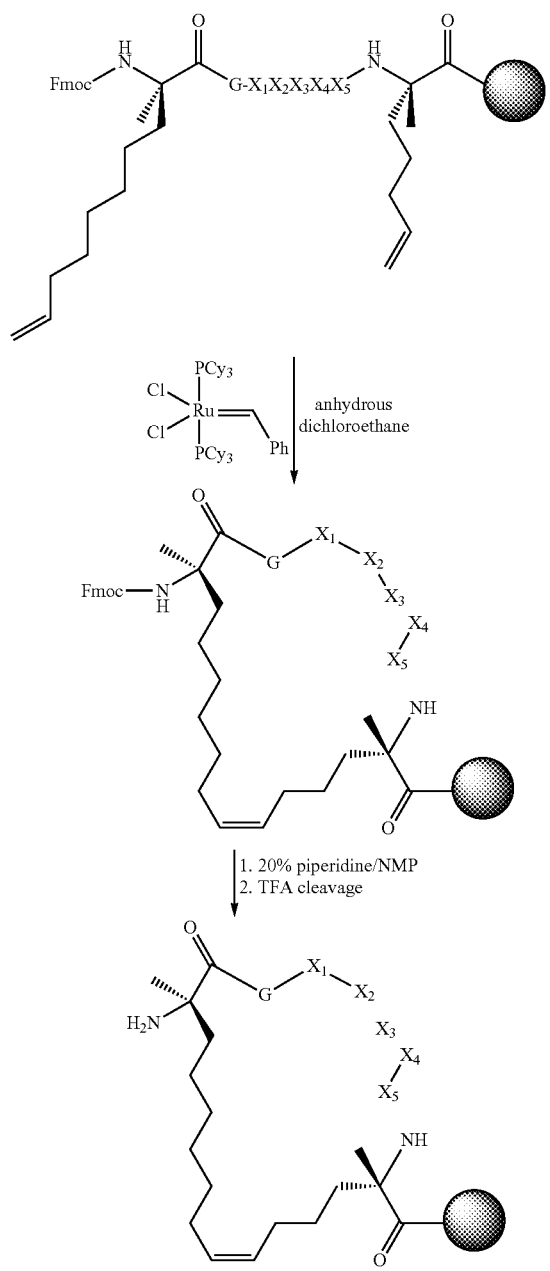

A linear library of the form Fmoc-R-$I_8$-G-$X_1X_2X_3X_4X_5$-S-$I_5$-TG, (R-$I_8$=R-2-amino-2methyldec-9-enoic acid), TG=Tentagel-S—$NH_2$ resin, S-$I_5$=S-2-amino-2methyldec-9-enoic acid, and Xi=D-Ala, D-Arg, D-Asn, D-Asp, D-Glu, D-Gln, Gly, D-His, D-Ile, D-Leu, D-Lys, D-Phe, D-Pro, D-D-Thr, D-Trp, D-Tyr, D-Val) was synthesized using standard solid phase techniques. The amino acid after S-$I_5$ was double coupled using standard SPPS protocols, to maintain the efficiency of the coupling step. The amino acid pair R-$I_8$ and S-$I_5$ were chosen for the RCM reaction, since R-$I_8$ and S-$I_5$, separated by 6 amino acids in a helical peptide, provides very effective crosslinking (98% yield). While a majority of the randomized OBOC peptides will not be of a helical form, the long alkyl cross linker (total 13 atoms) should enable the peptides to cyclize on bead via RCM. The on bead peptides were cyclized using Grubb's catalyst, bis(tricyclohexylphosphine)benzylidine ruthenium(IV) dichloride according to literature methods. Briefly, in an argon atmosphere, the peptide library R-$I_8$-G-$X_1X_2X_3X_4X_5$-S-$I_5$-TG was swelled for 30 minutes in anhydrous dichloroethane solution. 1 ml of 10 mM solution of the Grubb's catalyst in dichloroethane was added to the swelled resin and the reaction was allowed to proceed for 6 hours. The solution was drained and the reaction with the catalyst was repeated again for 6 hours. The library was washed with anhydrous dichloroethane and the excess catalyst was removed using oxine in DMF. The Fmoc group was removed by treatment with 20% piperidine/NMP. The library was washed and dried and the side chains were deprotected by treatment with 95:2.5:2.5 TFA/TES/$H_2O$. The final cyclized library was stored in TBS buffer.

Example 2

Synthesis of Triazole Cyclized OBOC Libraries

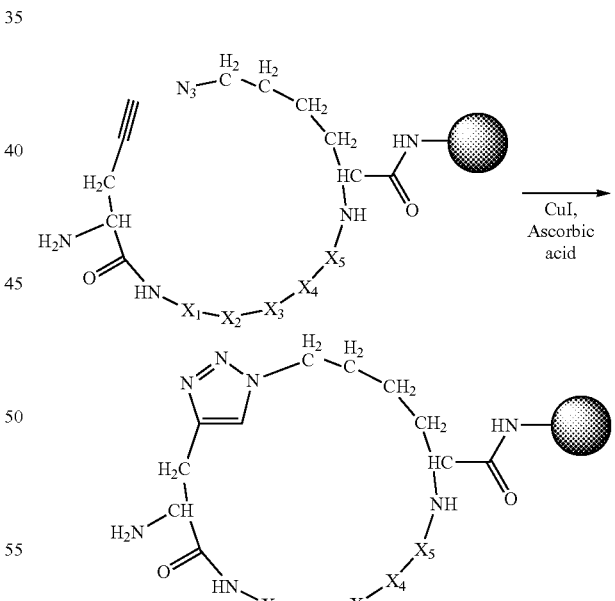

The linear peptide libraries A, B, C (Table 2) were synthesized on Tentagel-S—$NH_2$ resin using standard SPPS library synthesis methods. Libraries B and C were synthesized at a 10-fold excess to ensure adequate representation of each library element. After the synthesis of each library, all the beads in the linear library were subjected to an on bead CuAAC reaction, for 6 hours at room temperature with 1.5 equivalents of CuI, 2.5 equivalents of ascorbic acid in 20% piperidine in DMF. After washes with 10% sodium diethyldithiocarbamate in DMF to remove the adsorbed Cu, the library was washed with DMF, methanol and DCM and dried. Random beads were picked from the library to be sequenced. The rest of the library was stored in NMP until used. The structure and details of the three libraries are shown in the Table 2.

Example 3

Identification of Binding Agents for Akt2

Figure 5:
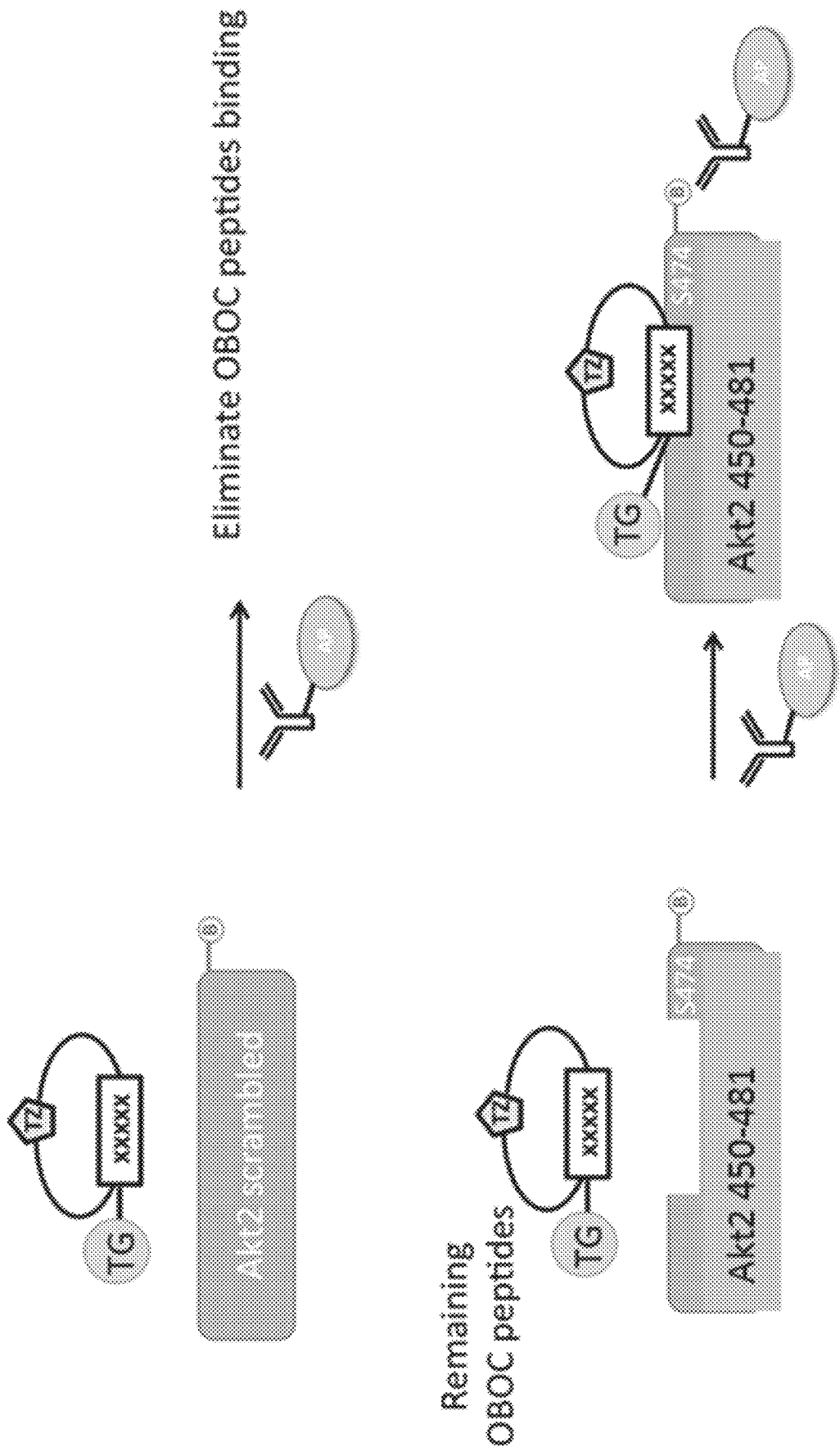
FIG. 5 is a schematic diagram showing an exemplary screening procedure for identification of binding agents for Akt2.

The peptide libraries of Example 2 were screened against the C-terminal epitope of Akt2 that contains residues 450-481 as illustrated in FIG. 5. Those residues include the phosphorylation site S474 which, for the screen exemplified in this example, was phosphorylated. The peptide libraries were first screened against synthetic peptide that represented a scrambled epitope of Akt2 450-481 to eliminate those library elements that bind to closely related epitopes. The remaining library elements were screened against a synthetically prepared polypeptide fragment representing the phosphorylated Akt2 C-terminus. The libraries A, B, C (from example 2) were all screened. Library C yielded hits, and the sequence of those hits (determined by Edman degradation) is shown in Table 3 (Tz4 indicates 4-carbon linker to

TABLE 2

Cyclic Peptide Libraries

| Library No. | Sequence | Amino acids used | Number of unique sequences |
|---|---|---|---|
| A  Cy(Pro-$X_1X_2X_3X_4X_5X_6X_7$-Tz4) | [cyclic peptide structure with Pro, $X_1$–$X_7$, and triazole linker to bead] | $X_i$ = D-Ala, Gly, D-Leu, D-Ile, D-Val, D-Phe, D-Trp, D-Arg, D-His, D-Lys, D-Asp, D-Glu, D-Asn, D-Gln, D-Ser, D-Thr, D-Tyr, D-Pro. | 612,220,032 |
| B  Cy($X_1X_2X_3X_4X_5$-Tz4) | [cyclic peptide structure with $X_1$–$X_5$ and triazole linker to bead] | $X_i$ = D-Ala, Gly, D-Leu, D-Ile, D-Val, D-Phe, D-Trp, D-Arg, D-His, D-Lys, D-Asp, D-Glu, D-Asn, D-Gln, D-Ser, D-Thr, D-Tyr, D-Pro. | 1889568 |
| C  Cy($X_1X_2X_3X_4X_5$-Tz4) | [cyclic peptide structure with $X_1$–$X_5$ and triazole linker to bead] | $X_i$ = L-Ala, Gly, L-Leu, L-Ile, L-Val, L-Phe, L-Trp, L-Arg, L-His, L-Lys, L-Asp, L-Glu, L-Asn, L-Gln, L-Ser, L-Thr, L-Tyr, L-Pro. | 1889568 |

FIG. 4 provides a summary of the above prepared libraries and data for an exemplary cyclic peptide. As shown in FIG. 4, the variable region 8 of the library peptides comprises either 5 or 7 amino acids, selected from either the D or L stereoisomers of the natural 20 amino acids, excepting cysteine and methionine. When a particular peptide is prepared and cyclized using Cu-catalyzed click chemistry, the signature of a free azide 6 in the non-cyclized peptide, which appears in the infrared absorption spectrum at 2100 cm$^{-1}$ 40, disappears.

triazole). Note that the sequence order reflects that expected from the cyclic peptide sequencing designed as shown in FIG. 2.

TABLE 3

Sequence of Hits Against Akt2

| $X_1$ | $X_2$ | $X_3$ | $X_4$ | $X_5$ | $X_6$ | $X_7$ |
|---|---|---|---|---|---|---|
| — | Y | V | Y | K | S | $Tz_4$ |
| — | V | F | A | K | V | $Tz_4$ |
| — | I | R | Y | Y | S | $Tz_4$ |
| — | Y | Y | T | Y | T | $Tz_4$ |

Figure 6:
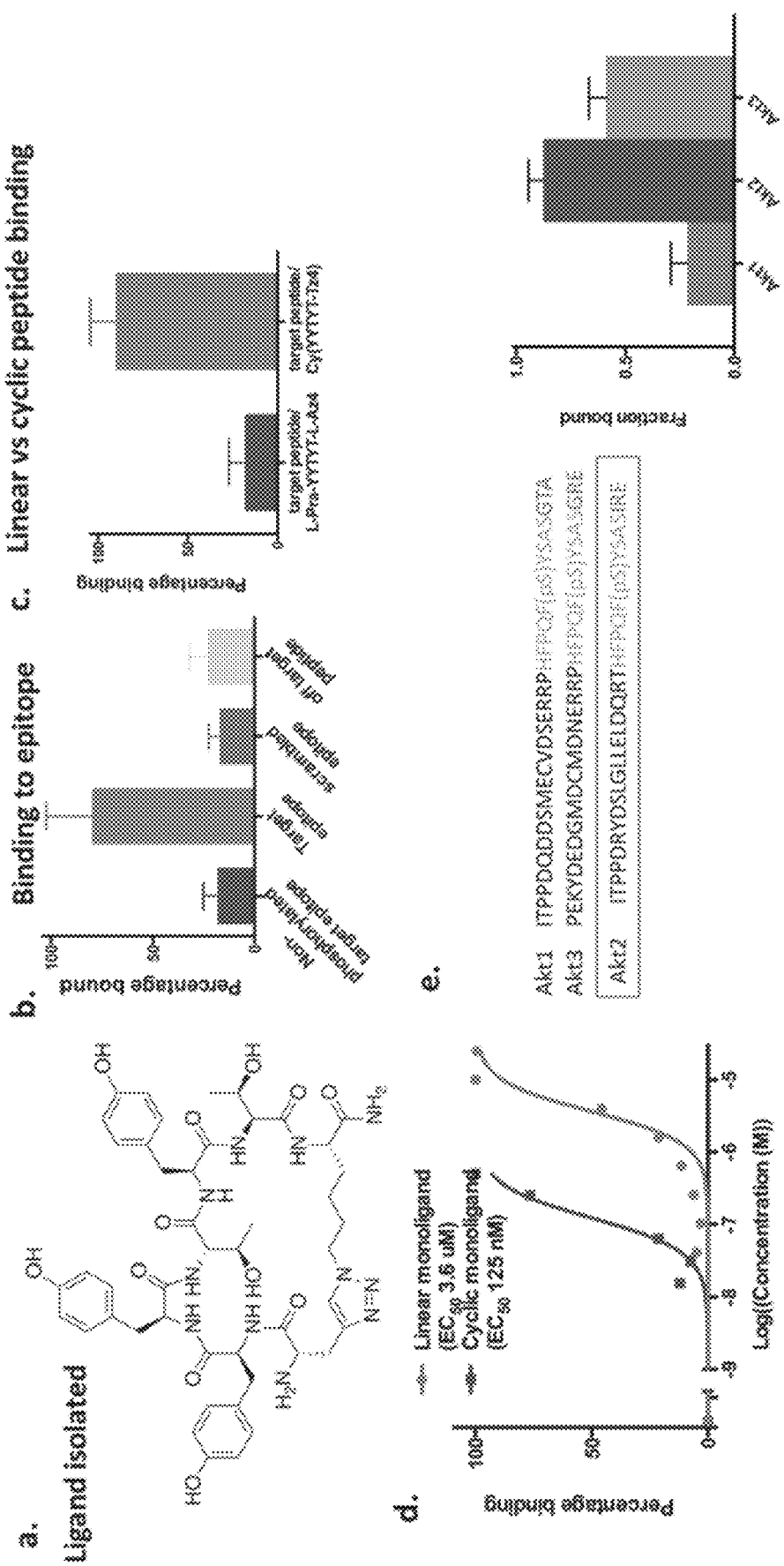
FIG. 6A shows the structure of an exemplary Akt2 binding agent.
FIG. 6B is binding data for an exemplary Akt2 binding agent.
FIG. 6C presents data comparing binding of a cyclic versus linear peptide.
FIG. 6D is a graph comparing binding of a cyclic versus linear peptide.
FIG. 6E shows the Akt target epitope sequences and binding data for Akt1, Akt2 and Akt3.

The structure of an isolated hit, with sequence of variable region YYTYT (SEQ ID NO: 4) is illustrated in FIG. 6a. FIG. 6b shows data for a single point immunoassay showing relative selectivity of the hit against the targeted epitope, versus scrambled epitope, non-phosphorylated target epitope, and off-target peptide. FIG. 6c is a single point immunoassay illustrating the improved binding of the target cyclic peptide (Cy(YYTYT (SEQ ID NO: 4)-Tz4)) relative to the linear variant thereof. FIG. 6d is an affinity estimation from immunoassays in which the Cy(YYTYT (SEQ ID NO: 4)-Tz4) peptide is compared against the corresponding linear peptide for capturing full-length Akt2 protein. The cyclic peptide exhibits a 30-fold higher affinity. Finally, FIG. 6e presents selectivity assay data showing the relative binding of the cyclic peptide to the Akt2 protein, relative to the closely related Akt1 and Akt3 proteins. The sequence of the C-terminal regions for all three proteins is given.

The hit isolated from library C was used in further screening to identify biligand binding agents for Akt2 according to the methods described above. Namely, the cyclic peptide hit was modified to contain an azide moiety at the $R^3$ position. The azide modified peptide bound to its Akt2 binding site was screened against a peptide library presenting an alkyne moiety. Biligand hits were identified by formation of an in situ click product (azide).

Biligand hits are presented in FIG. 7. As shown in FIG. 7, the biligand hits have high affinity for Akt2 and both hits had significantly higher affinity than the monoligand.

Example 4

Identification of Binding Agents for pfLDH and pvLDH

Figure 9:
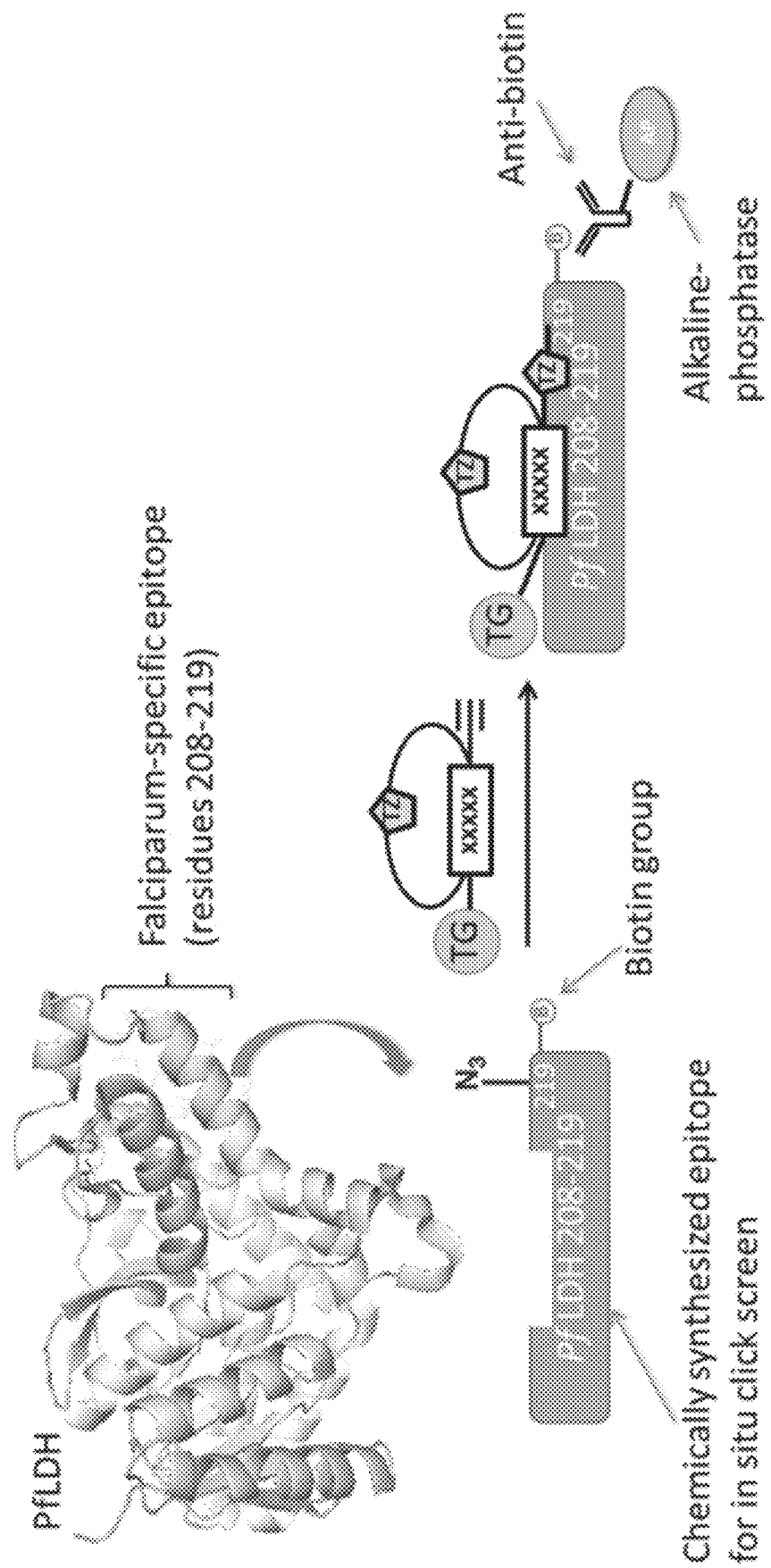
FIG. 9 illustrates and exemplary procedure for identification of primary binding agents for pfLDH.

A peptide library for screening against pfLDH and pvLDH epitopes (FIG. 8) was prepared and screened as illustrated in FIG. 9. This example utilizes in situ click epitope targeting strategy to identify cyclic peptide ligands that can specifically detect pfLDH for the *Plasmodium falciparum* subspecies. The peptide epitope LISDAELEAIFD (SEQ ID NO: 34) is specific for the *Plasmodium falciparum* LDH protein. For the PfLDH specific screen, a synthetic peptide representing the targeted epitope, with an azide-presenting amino acid in place of the native amino acid, was prepared with a PEG linker and a biotin tag. The target sequence used in the screen was LISDAELEAIFD (SEQ ID NO: 34)-Az4-PEG-Biotin. The 5mer cyclic peptide library (table 2, library C) was then designed to present an acetylene group at the N terminal (see e.g., FIG. 1). The library was first screened against the sequence DDIAILEEFALS (SEQ ID NO: 35)Az4-PEG-Biotin, a scrambled version of the epitope. The peptide binders to this scrambled version were eliminated. The rest of the library was stripped of protein and then rescreened against the target epitope LISDAELEAIFD (SEQ ID NO134)-Az4-PEG-Biotin and the cyclic peptides that formed triazole linkages to the synthetic peptide epitope were identified. (see FIG. 1 and Example 1). Hit sequences are provided Table 4.

TABLE 4

Sequence of Hits Against LDH

| Hit | Residue 1 | 2 | 3 | 4 | 5 | 6 | 7 | 8 |
|---|---|---|---|---|---|---|---|---|
| 1 | L-Pra | link (Tz) | R | G | G | I | L | link (Tz) |
| 2 | L-Pra | link (Tz) | K | K | II | H | L | link (Tz) |
| 3 | L-Pra | link (Tz) | I | L | Y | W | K | link (Tz) |
| 4 | L-Pra | link (Tz) | P | L | K | K | G | link (Tz) |
| 5 | L-Pra | link (Tz) | L | K | T | G | Q/T | link (Tz) |
| 6 | L-Pra | link (Tz) | H | W | S | A | N | link (Tz) |
| 7 | L-Pra | link (Tz) | Y | W | Q | W | — | link (Tz) |

Figure 10:
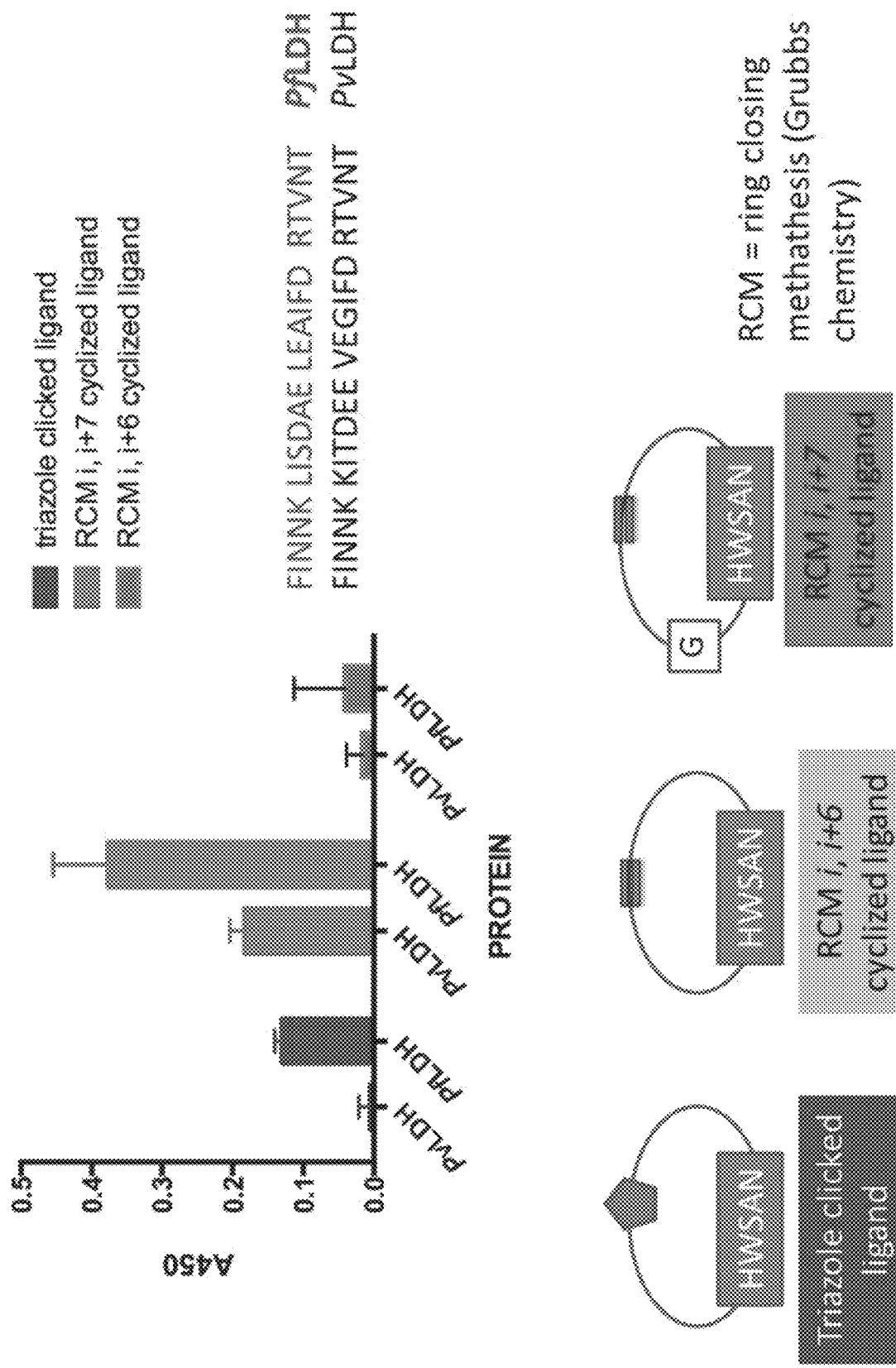
FIG. 10 presents binding data for three exemplary pLDH binding agents and provides data comparing pfLDH binding versus pvLDH binding.

Hit sequence No. 6 (HWSAN (SEQ ID NO: 11)) was identified for further testing against the whole PfLDH or PvLDH proteins, results of which are presented in FIG. 10. As seen in FIG. 10, the HWSAN (SEQ ID NO: 11) peptide has high affinity for both LDH variants. A RCM cyclized version of the HWSAN (SEQ ID NO: 11) peptide was synthesized. 5 uM of the biotinylated ligands were immobilized on a streptavidin plate, blocked with 5% milk and then treated with GST-PfLDH or GST-PvLDH proteins overnight. The binding was detected using antiGST-HRP antibody. Note that the RCM cyclic peptide exhibits higher affinity for PfLDH, while the triazole-cyclized peptide exhibits higher selectivity between the PfLDH and PvLDH.

Figure 11:
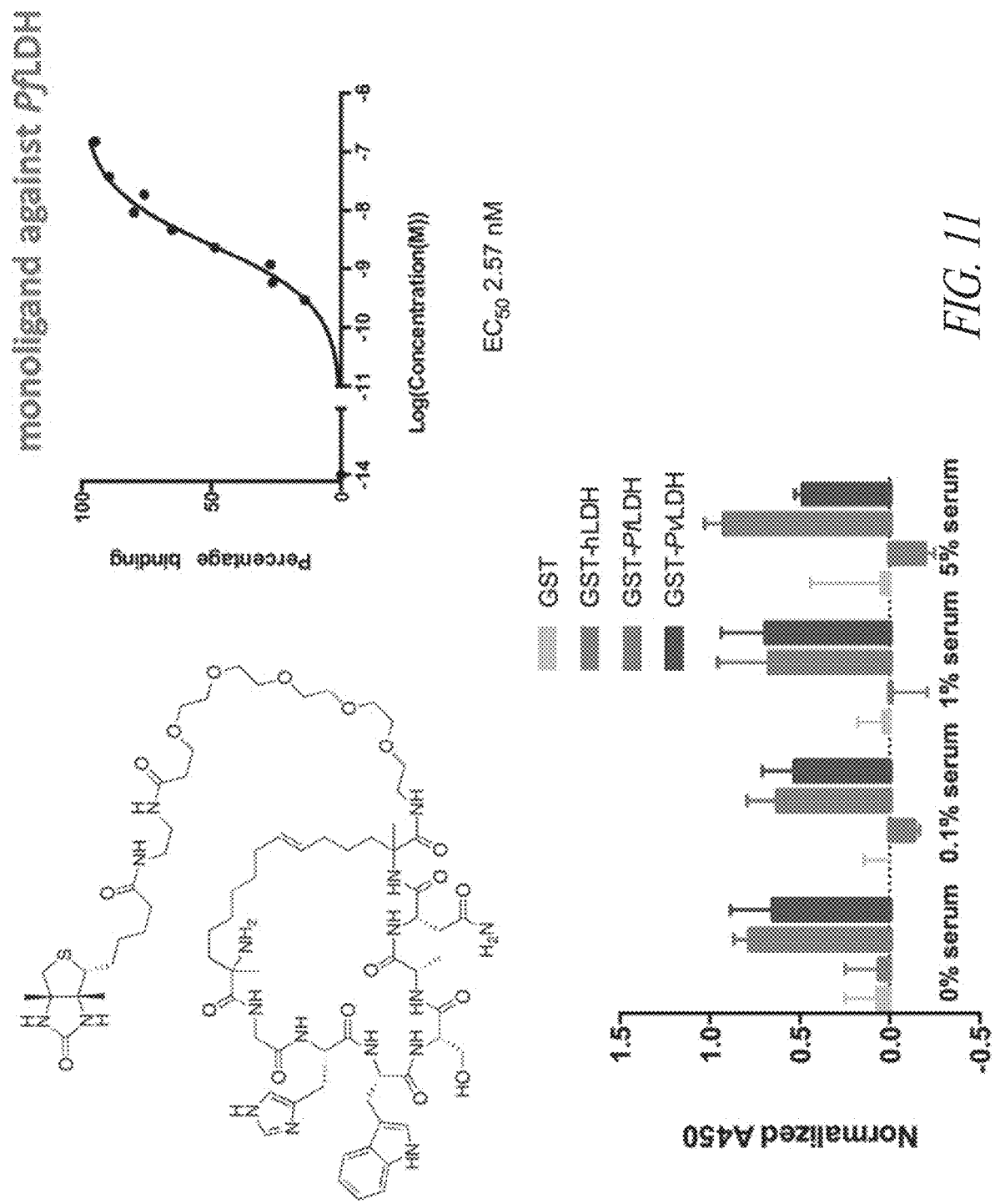
FIG. 11 provides the structure and binding data for an exemplary monoligand pfLDH binding agent.

FIG. 11 presents data for one of the RCM cyclized peptides, which shows high affinity for the PfLDH protein with an EC50 of 2.5 nM. To look at the selectivity of the ligand, a single point ELISA was done with the biotinylated ligand immobilized on the streptavidin plate and treating with 10 nM PfLDH or PvLDH protein in varying concentrations of human serum.

Example 5

Identification of Alternate Binding Agents for pfLDH and pvLDH

This example utilizes in situ click epitope targeting strategy to identify cyclic peptide ligands that can detect a generic *Plasmodium* LDH protein, irrespective of subspecies, or specifically detect pfLDH for the *Plasmodium falciparum* subspecies. The peptide epitope GVEQVIELQLN (SEQ ID NO: 36) is conserved across all strains of malarial parasite LDH. For development of a capture agent that identifies all pLDH protein, a linear peptide library was screened against this conserved region of pLDH (amino acid residues 285-295, FIG. 8) utilizing the in situ click epitope targeting strategy to identify a primary ligand hevwh. The primary linear ligand was modified to include an alkyne moiety at the C-terminus and this modified ligand was used in the screen of a cyclic peptide library C in Table 2 modified with an azide moiety in the presence of pfLDH as described herein. The library was anti-screened against human serum to remove the library components that non-specifically bind to serum proteins. Binary binding agents were identified by formation of a triazole bond between the primary ligand and members of the cyclic peptide library. Hit sequences are provided in Table 5.

TABLE 5

Sequence of Hits Against pan pLDH

| Hit | Residue 1 | 2 | 3 | 4 | 5 | 6 | 7 |
|---|---|---|---|---|---|---|---|
| 1 | Az4 | Link (Tz) | Y | L | G | H | K |
| 2 | Az4 | L | | A | Y | P/A | P/A | Az4 |
| 3 | Az4 | Link (Tz) | E | L | Y | K | Y |

The structure of the resulting binary ligand hevwh-YLGHK based on the hit sequence No. 1 and representative data is presented in FIG. 11. This binary ligand showed high affinity for both pf- and pvLDH in sandwich ELISAs using NeutrAvidin-coated microtiter plates loaded with biotinylated ligand and incubated with varying concentrations of pLDHs in TBS (FIG. 11 B). Similar ELISA was performed with pLDHs and human LDH (hLDH) in the presence of 1 and 5% (v/v) human serum to confirm the selectivity and high activity of the binary ligand in complex mixtures.

Example 6

Identification of Binding Agents for Histidine Rich Protein (HRP)II Ligand

Figure 13:
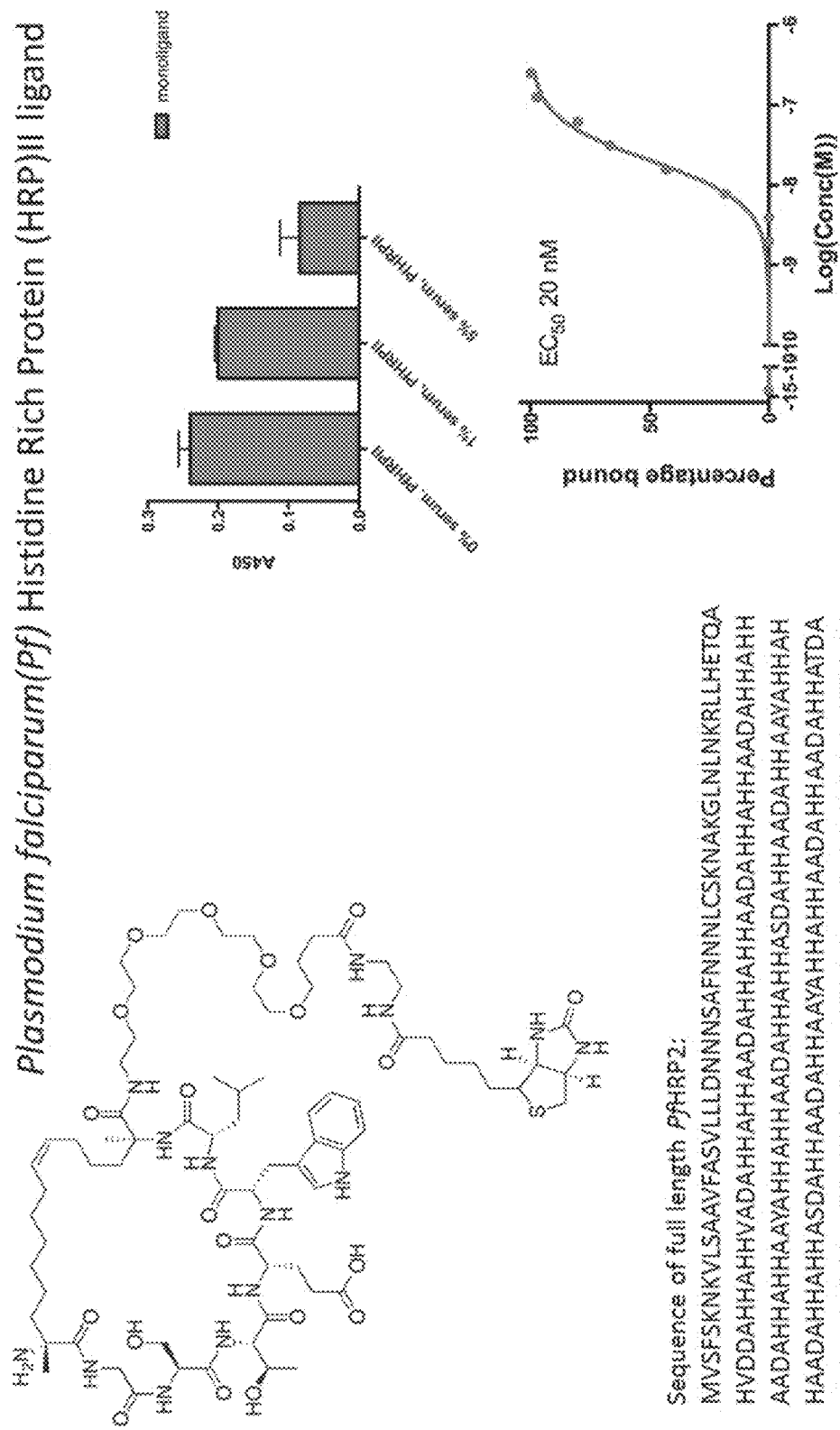
FIG. 13 presents the structure, targeted epitope and binding data for an exemplary pfHRP(II) binding agent.

A metathesis cyclic peptide library prepared as described above (example 1) was modified with an azide handle at the N terminal and screened against the conserved C terminal region of the PfHRP2 protein as illustrated in FIG. 13. The library is first screened against the N terminal sequences MVSFSKNKVLSAAVFASVLLLDNNNS (SEQ ID NO: 37)-L-Pra-PEG-biotin and L-Pra-FNNNLCSKNAKGLNLNKRLLHETQ AHVDD (SEQ ID NO: 38)-PEG-biotin using methods analogous to those described above. The binders to the N terminal sequences were removed and the rest of the library was screened against the conserved C terminal sequence modified with an alkyne tag, AHHATDAHHAAAHHEAATHC (SEQ ID NO: 39)(L-Pra)RH-PEG-biotin. The sequences binding to the target sequence via the click reaction were sequenced via Edman and are represented in table 6.

TABLE 6

Sequence of Hits Against PfHRP2

| Az4 | — | G | X1 | x2 | x3 | x4 | x5 | — |
|---|---|---|---|---|---|---|---|---|
| Az4 | — | G | I | F | A | V | T | — |
| AZ4 | — | G | I | V | G | A | P | — |
| AZ4 | — | G | N | W | P | A | A | — |
| AZ4 | — | G | F/W | N | V | D | L | — |
| AZ4 | — | G | S | T/Q | E | W | L | — |
| AZ4 | — | G | T | E | S | V | A | — |
| AZ4 | — | G | Q/T | I | T/Q | I | Y | — |
| AZ4 | — | G | T/Q | A | V | N | A | — |

The structure of one of the hits and representative data is presented in FIG. 12. The biotinylated peptide was immobilized on a streptavidin plate and titrated with varying concentrations of the PfHRP2 protein, to yield an $EC_{50}$ of 20 nM. For the selectivity assay, the effect of binding of the ligand to the PfHRP2 protein with varying serum concentrations was determined.

All of the U.S. patents, U.S. patent application publications, U.S. patent applications, foreign patents, foreign patent applications and non-patent publications referred to in this specification are incorporated herein by reference, in their entirety to the extent not inconsistent with the present description.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A cyclic peptide having the following structure (I):

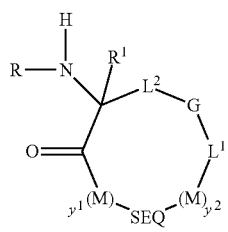

or a salt, tautomer or stereoisomer thereof, wherein:
- $L^1$ and $L^2$ are each individually optionally substituted linker moieties, each linker moiety optionally comprising a linkage to a solid support, a linkage to a reporter moiety, a linkage to a peptide ligand, a linkage to an azide or alkyne moiety or combinations thereof;
- G is a triazole;
- M is methionine;
- R is H, $-L^3$-A or C(=O)-$L^3$-A, wherein $L^3$ is a linker moiety and A is an alkyne or an azide, or wherein $L^3$ is a linker moiety comprising triazole and A is a bond to a peptide ligand;
- $R^1$ is H or $C_1$-$C_6$ alkyl;
- $y^1$ and $y^2$ are each individually 0 or 1; and
- SEQ is an amino acid sequence comprising from 2 to 20 amino acids selected from the group consisting of: D-alanine, glycine, D-leucine, D-isoleucine, D-valine, D-phenylalanine, D-tryptophan, D-arginine, D-histidine, D-lysine, D-aspartate, D-glutamate, D-asparagine, D-glutamine, D-serine, D-threonine, D-tyrosine, D-proline, L-alanine, L-leucine, L-isoleucine, L-valine, L-phenylalanine, L-tryptophan, L-arginine, L-histidine, L-lysine, L-aspartate, L-glutamate, L-asparagine, L-glutamine, L-serine, L-threonine, L-tyrosine, L-proline, hydroxyproline, carboxyglutamate, O-phosphoserine, homoserine, norleucine, methionine sulfoxide, and methionine methyl sulfonium.

2. The cyclic peptide of claim 1, wherein $L^1$, $L^2$, or both, comprise one or more substituents selected from alkyl, alkyne, azide and aminocarbonyl.

3. The cyclic peptide of claim 1, wherein $L^1$, $L^2$, or both, comprise a linkage selected from a linkage to a solid support, a linkage to a reporter moiety and a linkage to a peptide ligand.

4. The cyclic peptide of claim 1, wherein $L^1$ and $L^2$ are alkylene.

5. The cyclic peptide of claim 1, wherein the cyclic peptide has the following structure (Ia):

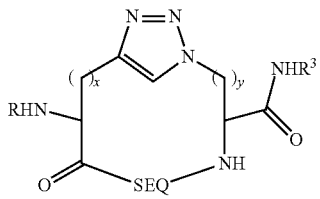

wherein:
- $R^3$ is H, a linkage to a solid support, a linkage to a reporter moiety, a linkage to a peptide ligand, a linkage to an azide or alkyne moiety or combinations thereof; and
- x and y are each independently an integer from 1 to 8.

6. The cyclic peptide of claim 1, wherein SEQ comprises from 2 to 9 amino acids.

7. The cyclic peptide of claim 6, wherein SEQ comprises from 5 to 7 amino acids.

8. The cyclic peptide of claim 1, wherein the amino acids are selected from D and L stereoisomers of Ala, Gly, Leu, Ile, Val, Phe, Trp, Arg, His, Lys, Asp, Glu, Asn, Gln, Ser, Thr, Tyr and Pro.

9. The cyclic peptide of claim 1, wherein R is H or —C(=O)-$L^3$-A, where $L^3$ is a linker moiety and A is a bond to a peptide ligand or an alkyne.

10. The cyclic peptide of claim 9, wherein A is an alkyne.

11. The cyclic peptide of claim 1, wherein SEQ has 90% sequence identity to an amino acid sequence comprising any one of SEQ ID NOS: 1-33.

12. The cyclic peptide of claim 11, wherein SEQ comprises any one of SEQ ID NOS: 1-14.

13. The cyclic peptide of claim 1, wherein $y^1$ and $y^2$ are each 0.

14. A composition comprising the cyclic peptide of claim 1 and a pharmaceutically acceptable carrier.

15. The cyclic peptide of claim 1, wherein the cyclic peptide comprises a linkage to a reporter moiety, the reporter moiety selected from polyethylene glycol (PEG), biotin, thiol and fluorophores.

16. The cyclic peptide of claim 15, wherein the fluorophores are selected from carboxyfluorescein (FAM), fluorescein isothiocyanate (FITC), Cyanine-5 (Cy5), tetramethylrhodamine (TRITC) and Carboxytetramethylrhodamine (TAMRA).

17. The cyclic peptide of claim 7, wherein the amino acids are selected from D and L stereoisomers of Ala, Gly, Leu, Ile, Val, Phe, Trp, Arg, His, Lys, Asp, Glu, Asn, Gln, Ser, Thr, Tyr and Pro.

* * * * *